(12) United States Patent
Makeev et al.

(10) Patent No.: US 12,130,245 B2
(45) Date of Patent: Oct. 29, 2024

(54) VARIABLE ZOOM X-RAY COMPUTED TOMOGRAPHY METHOD FOR COMPOSITES

(71) Applicant: BOARD OF REGENTS, THE UNIVERSITY OF TEXAS SYSTEM, Austin, TX (US)

(72) Inventors: Andrew Makeev, Dallas, TX (US); Yuriy Nikishkov, Dallas, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 271 days.

(21) Appl. No.: 17/766,637

(22) PCT Filed: Oct. 9, 2020

(86) PCT No.: PCT/US2020/055030
§ 371 (c)(1),
(2) Date: Apr. 5, 2022

(87) PCT Pub. No.: WO2021/072229
PCT Pub. Date: Apr. 15, 2021

(65) Prior Publication Data
US 2022/0381705 A1 Dec. 1, 2022

Related U.S. Application Data

(60) Provisional application No. 62/913,775, filed on Oct. 11, 2019.

(51) Int. Cl.
*G01N 23/046* (2018.01)
*A61B 6/03* (2006.01)

(52) U.S. Cl.
CPC ........... *G01N 23/046* (2013.01); *A61B 6/032* (2013.01); *G01N 2223/401* (2013.01); *G06T 2207/20048* (2013.01)

(58) Field of Classification Search
CPC ........... G01N 23/046; G01N 2223/401; G01N 2223/615; A61B 6/032; G06T 2207/20048
(Continued)

(56) References Cited

U.S. PATENT DOCUMENTS 8,548,117 B2 * 10/2013 Noordhoek .......... A61B 6/4233
378/11
10,251,613 B2 * 4/2019 Allmendinger ...... A61B 6/4014
(Continued)

FOREIGN PATENT DOCUMENTS

CA 2949252 A1 * 9/2014 ......... A61B 1/00059
JP 2001299738 A * 10/2001 ............. A61B 6/027
(Continued)

OTHER PUBLICATIONS

International Search Report in Application No. PCT/US2020/055030, mailed Jan. 27, 2021, 7 page.
(Continued)

*Primary Examiner* — Mahendra R Patel
(74) *Attorney, Agent, or Firm* — Meunier Carlin & Curfman LLC

(57) ABSTRACT

A variable zoom X-ray CT method can significantly improve resolution for structures with large in-plane dimensions, for example to detect complex structural damage due to low-velocity impact in large thin composite laminate panels. The variable zoom method comprises emitting an X-ray beam from an X-ray source to project a region of interest (ROI) of a specimen within a field of view (FOV) onto a detector. Projections of the ROI are scanned with the detector while rotating the specimen about a rotational axis of a specimen stage and translating the specimen stage along an acquisition trajectory between the X-ray source and the detector. The acquisition trajectory specifies a source-to-object distance
(Continued)

(SOD) between the X-ray source and the rotational axis of the specimen stage at each rotation angle of the specimen stage. A reconstruction computer reconstructs a three-dimensional volume of the specimen from the projections scanned by the detector.

19 Claims, 16 Drawing Sheets

(58) Field of Classification Search
USPC .......................................................... 382/141
See application file for complete search history.

(56) References Cited

U.S. PATENT DOCUMENTS

| | | | | |
|---|---|---|---|---|
| 11,954,769 | B2* | 4/2024 | Bontus | ................... G06T 11/005 |
| 2010/0121183 | A1* | 5/2010 | Taguchi | ................ G06T 11/006 |
| | | | | 382/131 |
| 2012/0014582 | A1* | 1/2012 | Schaefer | ................ A61B 6/032 |
| | | | | 382/131 |
| 2012/0301004 | A1* | 11/2012 | Kingston | ............. G01N 23/046 |
| | | | | 382/131 |
| 2014/0233691 | A1* | 8/2014 | Sheppard | .............. G06T 11/006 |
| | | | | 378/4 |
| 2014/0233692 | A1* | 8/2014 | Case | ................... G06F 3/04842 |
| | | | | 715/781 |
| 2017/0340287 | A1* | 11/2017 | Fulton | ..................... A61B 5/721 |
| 2019/0323946 | A1* | 10/2019 | Myers | ........................ G06T 7/20 |
| 2020/0170590 | A1* | 6/2020 | Gagnon | ................. A61B 6/405 |

FOREIGN PATENT DOCUMENTS

| | | | | | |
|---|---|---|---|---|---|
| JP | | 2004160218 | A * | 6/2004 | ............. A61B 6/027 |
| JP | | 3866431 | B2 * | 1/2007 | ............. A61B 6/027 |
| JP | | 2008055171 | A * | 3/2008 | ............. A61B 6/032 |
| JP | | 2020-173175 | A | 10/2020 | |
| JP | | 7198457 | B2 * | 1/2023 | ........... G01N 23/041 |
| WO | WO-2005091227 | A1 * | 9/2005 | ........... G06T 15/503 |
| WO | WO-2008156764 | A1 * | 12/2008 | ........... A61B 6/5264 |
| WO | WO-2013068987 | A1 * | 5/2013 | ............. A61B 6/022 |
| WO | WO-2013161443 | A1 * | 10/2013 | ........... G06T 11/006 |

OTHER PUBLICATIONS

Office Action in corresponding Japanese in Application No. 2022-521454 mailed May 27, 2024.

* cited by examiner

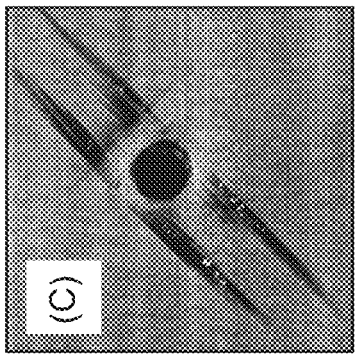
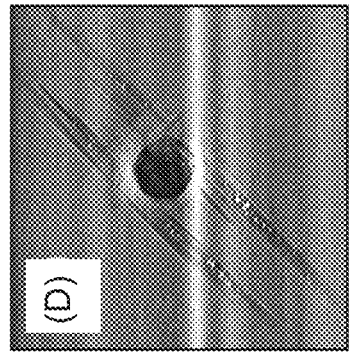
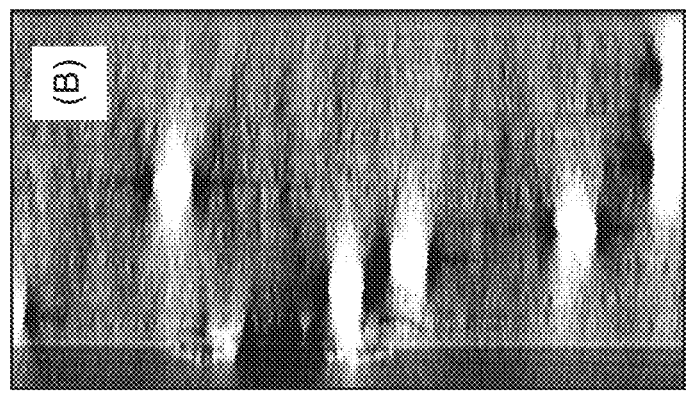
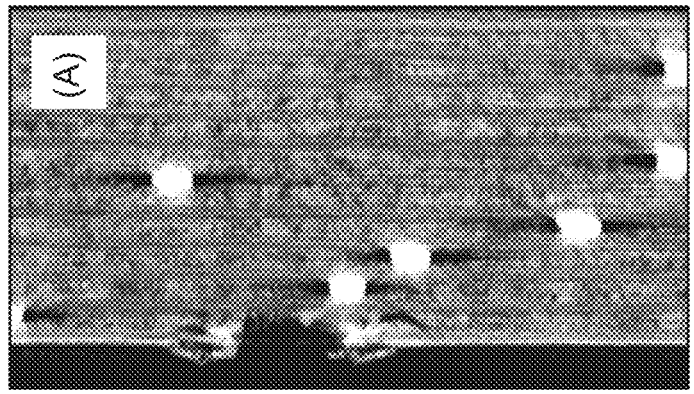

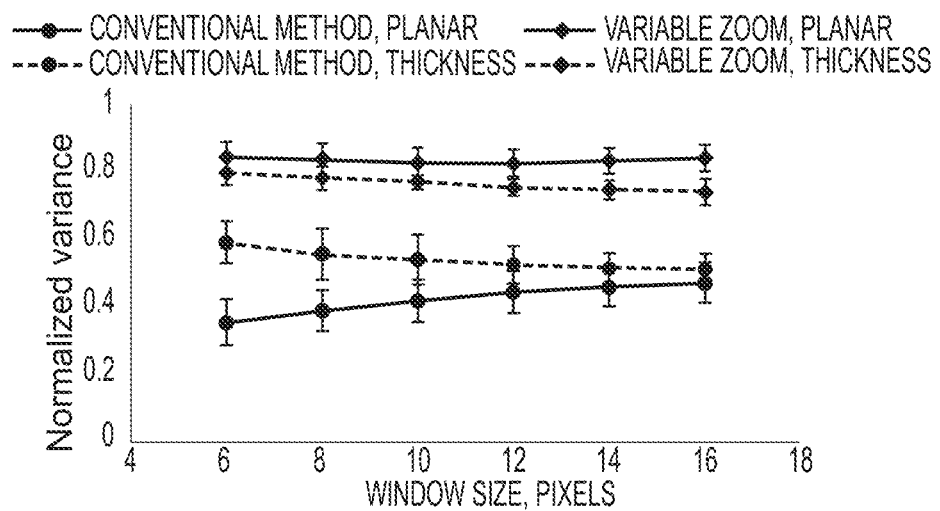
FIG. 21
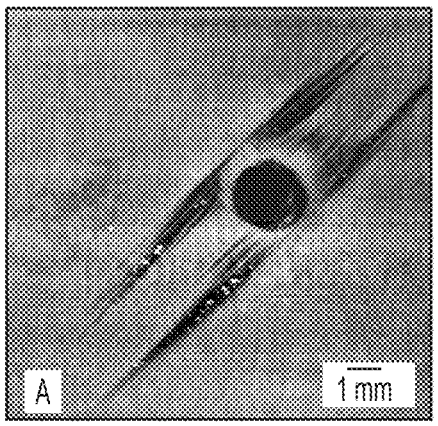
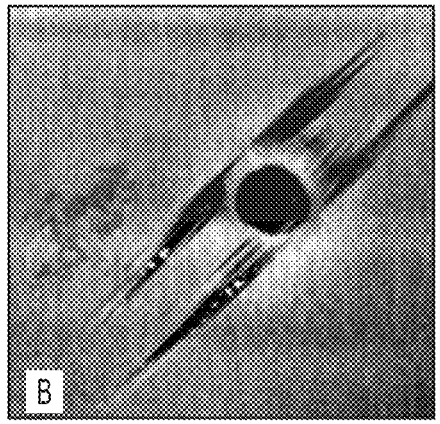
FIG. 22A　　FIG. 22B
FIG. 22C　　FIG. 22D

VARIABLE ZOOM X-RAY COMPUTED TOMOGRAPHY METHOD FOR COMPOSITES

CROSS REFERENCE TO RELATED APPLICATIONS

This application is a United States National Phase Patent Application of International Patent Application Number PCT/US2020/055030, filed on Oct. 9, 2020, which claims the benefit of priority to U.S. Application No. 62/913,775, filed Oct. 11, 2019, which are incorporated by reference herein in their entireties.

STATEMENT REGARDING FEDERALLY SPONSORED RESEARCH

This invention was made with government support under grant number W911NF-17-2-0195 awarded by the Army Research Laboratory. The government has certain rights in the invention.

BACKGROUND

The complexity of critical manufacturing defects and structural damage modes in polymeric composites calls for high-resolution nondestructive evaluation capable of accurately measuring the location and shape of such flaws in three dimensions with adequate objectivity for interpretation free of human errors. X-ray Computed Tomography (CT) has proven its unprecedented objectivity for nondestructive inspection of polymeric composite structures. However, high-resolution nondestructive evaluation of small critical flaws in composite structures with large in-plane dimensions has been a fundamental challenge for CT techniques.

Composite aircraft are starting to dominate the commercial aircraft market with the production of Boeing 787 and Airbus 350 and expected upgrades of legacy systems. On the United States Department of Defense application side, Lockheed Martin has been ordered to produce more than 3,000 F-35 aircraft. Similarly, the US Army and Rotorcraft Industry are facing the Future Vertical Lift aviation challenge to replace more than 6,300 military vertical lift aircraft [1]. Advanced fiber-reinforced polymer-matrix composites are playing a major role in designing high-performance and lightweight aircraft structures. However, uncertainty remains for the useful life of the composite rotor and airframe structures due to the complexity of damage and failure mechanisms. Additionally, the susceptibility of composite structures to manufacturing irregularities, which may be precursors to structural damage, impose risks that require accurate structural diagnostics for risk mitigation [1-3].

In order to advance composite material qualification and aircraft structural certification, the analysis must capture manufacturing complexity and variability of flight critical components and structure. It is worth noting that the fidelity of the nondestructive inspection (NDI) needed to quantify the smallest flaws that would impact structural performance is key to structural diagnostics of composite parts [1]. However, the fidelity of NDI required to characterize such flaws in production composite parts is not yet adequate. Small individual flaws present at critical locations can dramatically affect strength and durability of composite structures [2-3]. The susceptibility to manufacturing irregularities in the form of fiber-waviness and voids at ply interfaces, degrading residual strength and fatigue behavior; as well as complexity of structural damage modes and failure mechanisms are among the challenges in composites [4-6]. Assessment of structural integrity of composite elements depends on accurate detection of structural defect locations and voids at ply interfaces, degrading sizes leading to estimation of residual strength and after fatigue behavior; as well as complexity of structural or impact damage. Another challenge is the assessment of structural integrity of composite elements that depend on accurate detection of structural defect locations and sizes leading to estimation of residual strength after fatigue or impact damage [7-8]. Due to three-dimensional (3D) nature of the critical defects and damage modes, high-resolution nondestructive methods able to capture the location and geometry/shape of the individual flaws impacting structural performance are required.

X-ray Computed Tomography (CT) has proven its unprecedented objectivity for NDI of polymeric composites [9-11]. However, structures with large in-plane dimensions relative to thickness, typical in composite aircraft, are challenging for achieving adequate resolution required for accurately assessing the critical defects and damage modes. Modern industrial microfocus X-ray CT tomography systems are based on the cone-beam geometry, which uses a directional X-ray source that emits collimated cone X-ray beam (e.g., 30-degree wide) and projects the object on the flat panel detector, typically 8 to 16 inches (20-40 cm) in size. This setup allows CT systems to use geometric magnification of the object depending on how close the object is located to the source [12].

Impact damage has been the target of many studies by the X-Ray CT methods due to their advantages in 3D imaging of the damage topology. Reference [13] used the objectivity of X-ray CT data in all sections to reconstruct per-ply damage in curved laminate interfaces. A variety of X-Ray CT methods including Dual Energy CT, synchrotron radiations sources, and Computed Laminography were proposed to alleviate problem of large aspect ratio of the impacted panels, such as artifacts and noise related to incomplete data acquisition due to predominantly planar object size [14-15].

Despite the advances in CT, high-resolution 3D reconstruction of small defects in objects with large in-plane dimensions remains a fundamental challenge for the X-ray CT-based NDI. The current microfocus CT technology is based on full scanning (currently 360° around the object, or at least 180° plus cone beam angle [12]), which limits the applicability of the technology to small cross sections. Furthermore, even the objects, that can be scanned in the existing micro-CT facilities, may not allow for sufficient magnification of the composite structure if the resolution requirements place the inspected objects too close to the X-ray tube such that a full scan cannot be completed.

FIGS. 1A-1B illustrates object size limitations. For example, FIG. 1A shows a test article 102 with a large in-plane dimension relative to thickness. Rotation of the test article 102, shown in dotted lines, results in a collision between the test article 102 and a detector 104. Accordingly, the test article 102 may only be rotated through a limited range of projection angles. Reconstructions using limited ranges of projection angles below 180° in the industrial systems available today quickly lose the objectivity and oftentimes become erroneous during one-sided inspections, and often result in inconsistent 3D reconstructions associated with missing projections due to partial access. In another example, FIG. 1B shows a test article 106 placed too close to an X-ray tube 108. Rotation of the test article 106, shown in dotted lines, results in a collision between the test article 106 and the X-ray tube 108. Accordingly, the test article 106 may not be scanned at a desired magnification.

SUMMARY

A first aspect of the disclosure provides a variable zoom method of an X-ray computed tomography (CT) scanner. The method comprises emitting an X-ray beam from an X-ray source to project a region of interest (ROI) of a specimen within a field of view (FOV) onto a detector. The method comprises scanning projections of the ROI of the specimen with the detector while rotating the specimen about a rotational axis of a specimen stage and translating the specimen stage along an acquisition trajectory between the X-ray source and the detector. The method comprises reconstructing, by a reconstruction computer, a three-dimensional volume of the specimen from the projections scanned by the detector.

In some implementation of the first aspect of the disclosure, the X-ray source and the detector are stationary while rotating and translating the specimen.

In some implementation of the first aspect of the disclosure, the ROI is projected onto a central area of the detector.

In some implementation of the first aspect of the disclosure, the acquisition trajectory specifies a source-to-object distance (SOD) between the X-ray source and the rotational axis of the specimen stage at each rotation angle of the specimen stage.

In some implementation of the first aspect of the disclosure, the acquisition trajectory translates the rotational axis of the specimen stage along a center of the FOV.

In some implementation of the first aspect of the disclosure, an initial SOD along the acquisition trajectory is $SOD_{ROI}$, wherein the $SOD_{ROI}$ is a closest SOD at which the ROI is fully within the FOV.

In some implementation of the first aspect of the disclosure, the $SOD_{ROI}$ is a closest SOD at which the ROI remains within the FOV while a rotation angle of the specimen stage is less than a threshold angle.

In some implementation of the first aspect of the disclosure, the SOD at each rotation angle of the specimen stage is:

$$SOD(\theta) = \max\left\{SOD_{ROI}, S_0 + \frac{1}{2}(T_p + (S_p - T_p)|\sin\theta|)\right\},$$

where $\theta$ is the rotation angle of the specimen stage, SOD ($\theta$) is the SOD at each rotation angle of the specimen stage, $SOD_{ROI}$ is the initial SOD, $S_0$ is a safety offset, $S_P$ is a specimen width, and $T_P$ is a specimen thickness.

In some implementation of the first aspect of the disclosure, SOD ($\theta$)=$SOD_{ROI}$ while the rotation angle of the specimen stage is less than the threshold angle.

In some implementation of the first aspect of the disclosure, reconstructing the three-dimensional volume comprises weighting a backprojection of a set of filtered radiographs with a weighting factor based on the SOD at each rotation angle of the specimen stage.

In some implementation of the first aspect of the disclosure, the weighting factor comprises:

$$w^{yz}(\theta) = \frac{SOD(\theta)}{SDD},$$

where $w^{yz}$ is the weighting factor, SOD ($\theta$) is the SOD at each rotation angle of the specimen stage, and SDD is a source-to-detector distance.

In some implementation of the first aspect of the disclosure, reconstructing the three-dimensional volume further comprises calculating a projection to volume transformation for each projection angle and the SOD to produce the backprojection of the set of filtered radiographs. Reconstructing the three-dimensional volume further comprises and adding weighted backprojected pixel values to voxels in the three-dimensional volume based on an interpolation method to produce the reconstruction of the three-dimensional volume.

In some implementation of the first aspect of the disclosure, reconstructing the three-dimensional volume further comprises calculating a ramp filter in the frequency domain. Reconstructing the three-dimensional volume further comprises calculating weighted and filtered radiographs based on the ramp filter and applying a periodic-smooth decomposition to produce the set of filtered radiographs.

In some implementation of the first aspect of the disclosure, calculating the ramp filter in the frequency domain comprises calculating a one-dimensional direct Fourier Transform on:

$$h[np_x] = \frac{1}{(2p_x)^2}\begin{cases} 1, & n = 0 \\ 0, & n \text{ even} \\ -1/(\pi n/2)^2, & n \text{ odd} \end{cases},$$

where n is and integer $n \in [-n_x^{zp}, n_x^{zp}]$, $p_x$ is a row pixel spacing, $n_x^{zp}=(2n_x-1)_2$ rounded to the next power of two, and $n_x$ is a number of pixels in a projection row.

In some implementation of the first aspect of the disclosure, when calculating the projection to volume transformation, projection coordinates are different for each projection angle according to varying SOD($\theta$).

In some implementation of the first aspect of the disclosure, calculating the projection to volume transformation comprises:
calculating a three-dimensional coordinate transformation $(x, y, z)^T = R(\theta)R_{V'}\cdot(t, s, r)^T$, where (t, s, r) are reconstructed volume coordinates, (x, y, z) are projection coordinates, $R_V$ is a volume transformation matrix and $R_\theta$ is a matrix of specimen rotation.

In some implementation of the first aspect of the disclosure, the interpolation method is a distance-driven method or a separable footprints method.

In some implementation of the first aspect of the disclosure, the weighted and filtered radiographs are weighted to account for different ray lengths in a cone X-ray beam.

In some implementation of the first aspect of the disclosure, calculating the weighted and filtered radiographs and applying the periodic-smooth decomposition comprises calculating:

$$S_\theta(x, y_k) = [P'_\theta(x, y_k) * h(x)] = p_x IFFT\{FFTP'_\theta(x, y_k)_{ZP} \cdot FFTh[np_x]_{shift}\},$$

and $$P'_\theta(x, y_k) = PS\left[\frac{P_\theta(x, y_k)}{\sqrt{1 + (x^2 + y_k^2)/SOD^2(\theta)}}\right],$$

where FFT is a one-dimensional direct Fourier transform, IFFT is a one-dimensional inverse discrete Fourier transform, $h[np_x]_{shift}$ is a half-spaces of the ramp filter $h[np_x]$ swapped using a fftshift method, $n_x^{zp}$ is a zero-padded radiograph to avoid inter-period artefacts, and PS is the periodic-smooth decomposition such that only a periodic part of a weighted radiograph boundary is used.

In some implementation of the first aspect of the disclosure, adding the weighted backprojected pixel values to voxels in the three-dimensional volume based on an interpolation method comprises calculating:

$$v(t, s, r) = \Sigma_\theta w^{vz}(\theta) z_d^2(\theta) S_\theta(xz_d, yz_d),$$

where $$z_d(\theta) = \frac{1}{1 - z/SOD(\theta)},$$

$v(t, s, r)$ is a reconstruction volume value, the summation is calculated for all coordinate triads $(t, s, r)$, interpolated values $v(t, s, r)$ are obtained using the interpolation method, $w^{vz}(\theta)$ is the weighting factor, and $S_\theta(xz_d, yz_d)$ are filtered radiographs.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIGS. 13A-13D are reconstructed slices in an across-the-thickness direction and a through-thickness direction for the variable zoom using weighting and not using weighting.

FIG. 21 shows boundary unsharpness and normalized variance of impact defects.

FIGS. 22A and 22C show slices in a planar direction and through-the-thickness direction, respectively, for the Variable Zoom technique.

FIGS. 22B and 22D show slices in a planar direction and through-the-thickness direction, respectively, for the conventional method.

DETAILED DESCRIPTION

Figure 1A:
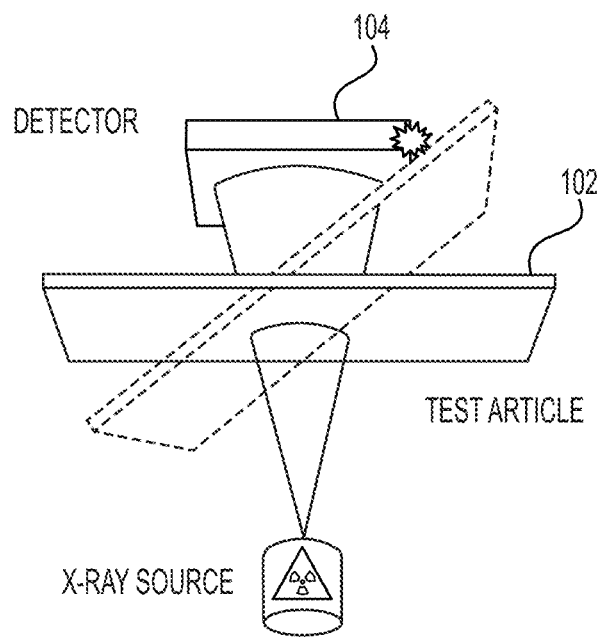
FIG. 1A is a simplified diagram of a CT system with a test article that is too large to make a full turn.
Figure 1B:
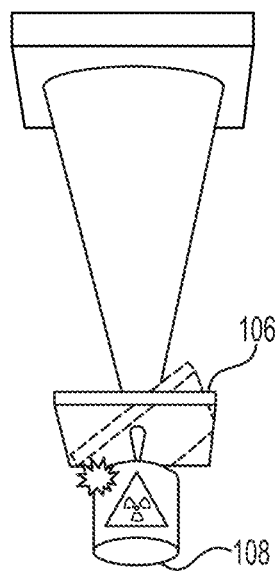
FIG. 1B is a simplified diagram of a CT system with a test article placed too close to an X-ray tube for a selected magnification.

It should be understood at the outset that although illustrative implementations of one or more embodiments are illustrated below, the disclosed systems and methods may be implemented using any number of techniques, whether currently known or in existence. The disclosure should in no way be limited to the illustrative implementations, drawings, and techniques illustrated below, but may be modified within the scope of the appended claims along with their full scope of equivalents. Use of the phrase "and/or" indicates that any one or any combination of a list of options can be used. For example, "A, B, and/or C" means "A", or "B", or "C", or "A and B", or "A and C", or "B and C", or "A and B and C".

Throughout the disclosure, references are made in superscripts to the documents in Reference List A below. For example, document 23 may be identified from Reference List A by placing the number twenty three in brackets [23].

Attempts to overcome size limitations for X-ray CT inspection can be grouped into two main categories: local tomography and limited-angle tomography. Local tomography deals with the scenario when a specimen does not constantly remain in the field of view (FOV) of the detector during scanning. This group of methods incorporates experimental techniques as well as improved analytical and iterative algorithms to overcome the presence of artifacts in the reconstructed volume due to truncated projections as discussed in detailed overview [13]. For example, a zoom-in technique has shown promising results for a parallel-beam X-ray geometry. The zoom-in technique is based on a combination of full-angle acquisition of high-resolution data in the FOV with full-angle low-resolution data for the entire specimen [25]. An experimental adaptive zooming technique, which uses a non-conventional scanning trajectory that keeps the specimen's region of interest (ROI) fully in the FOV, has also been proposed [26].

An alternative technique to local tomography is a limited-angle tomography. In some cases, a specimen width can be large enough that it becomes impossible to accommodate the entire specimen inside an X-ray CT system enclosure. Limited angle scanning techniques, although in general less accurate than full-angle CT, may present a potential solution. For instance, computed laminography, in which X-ray source and detector move synchronously irradiating a specimen at an inclined angle, was proposed as a promising NDT technique for objects with a large width-to-thickness aspect ratio [17]. The advantages and limitations of the computed laminography for the inspection of composites has been discussed in studies [22], [23]. Another possible technique refers to the case when projections are acquired from a limited projection angles. This leads to an ill-posed problem with a high number of artifacts deteriorating the resulting reconstruction quality. Despite the fact that limited-angle tomography helps overcoming geometric constraints related to large in-plane dimensions, current techniques are not capable of providing the same quality of the reconstructed volume as local and full-angle tomography.

Extensive research efforts have been undertaken to overcome the size limitations in X-ray CT. Published works encompass the development of nonconventional trajectories for radiograph acquisition combined with innovative reconstruction algorithms. One of the obvious solutions is the acquisition of projections in the limited-angle (<180°) range. However, the lack of projections in this acquisition leads a large number of artifacts deteriorating the reconstruction quality especially in through-the-thickness direction [16]. Computed Laminography (CL) is a well-known single-sided technique for identification of planar defects in flat objects, such as electronic boards, where X-ray source and a detector move synchronously irradiating a specimen at an inclined angle [17]. It has been shown to result in smaller artifacts as compared to limited-angle tomography [18]. CL implementation based on synchrotron radiation provides more methods to improve quality of defect detection [19] but cabinet system case studies have also been accomplished [20]. Evaluation of various CL trajectories and reconstruction methods specifically for composite NDT has been accomplished in studies [22-23]. Despite the improvement in overcoming geometric constraints related to large in-plane dimensions, CL is not capable to provide the same quality of the out-of-plane defect detection as the full-angle (360°) CT [21-23].

Another group of methods, local or Region-of-Interest (ROI) tomography, incorporates experimental techniques as well as improved algorithms to overcome the presence of artifacts due to features outside of ROI present in projections, which impair reconstruction quality even for the full-angle CT [24]. For example, the zoom-in technique based on a combination of full-angle acquisition of high-resolution data in the field of view (FOV) with full-angle low-resolution data for the entire specimen demonstrated accurate ROI reconstructions [25]. An experimental adaptive zooming technique, which uses a non-conventional scanning trajectory that keeps the specimen's ROI fully in the FOV, has been shown to result in increased spatial resolution [26]. While references [25-26] proposed similar radiograph acquisition trajectory to the trajectory proposed in this work, they neither aimed at nor showed through-the-thickness reconstruction quality improvement for laminated composites. Interlaminar failure has been a major challenge in laminated composite structures, hence the importance of detecting the associated defects and damage through the thickness.

Extensive research has been undertaken to overcome the size limitations in X-ray CT. Pioneering works emerged in the medical field attempting to reconstruct small-scale regions of interest (ROI) in human bodies, with later expansion to industrial CT. PenBel et al investigated modified 360° trajectory for ROI inspection of the partially accessible object. The unconventional scanning trajectory was driven by the size and shape of ROI continuously shifting a specimen as a function of a rotation angle. The findings showed that the proposed trajectory could achieve a high-fidelity scan in the area of interest on simulated 2D phantoms. Dabravolski et al used the acquisition trajectory following the convex hull of a specimen. The proposed Adaptive Zooming technique showed a superior reconstruction quality on the artificial data. MaaB et al tested several novel approaches combining data from low- and high-resolution scans to improve quality reconstruction. Kyrieleis et al have shown that extension of projections is suitable for reasonable approximation of the area of interest where high resolution is not required.

Computed Laminography (CL) is an alternative technique for large objects that cannot be accommodated in an X-ray CT system. The technique allows partial access to a test specimen by irradiating an object at an inclined angle. CL has been shown to result in smaller artifacts as compared to limited-angle tomography. Despite the improvement in overcoming geometric constraints related to large in-plane dimensions, CL is not capable to provide the same quality of the out-of-plane defect detection as the full-angle (360°) CT.

Disclosed herein is a variable zoom X-ray CT method able to overcome the limitations of large width-to-thickness aspect ratio in cabinet X-Ray CT systems and allow for additional flexibility in achieving high resolution for structures with large in-plane dimensions. The variable zoom method eliminates the need to destroy the inspection article by cutting out a small section enabling accurate inspection of the composite structure at sufficient magnification. Detection of complex structural damage, including accurate detection of through-the-thickness features, due to low-velocity impact in large and thin composite laminate panels, which is among the worst-case scenario for the conventional CT methods, demonstrates the accuracy of the variable zoom method. In addition to the variable zoom CT scanning approach, a novel convolution-backprojection reconstruction method is disclosed herein for achieving accurate high-resolution results. The disclosed technique includes two aspects: nonconventional radiograph acquisition trajectory and a modification to the industry-standard Feldkamp-Davis-Kress (FDK) reconstruction method that includes weighting of radiographs based on the distance from the panel to the X-ray source and enables higher quality of 3D reconstruction. The analysis of reconstruction quality of CT images produced by the Variable Zoom technique, including dimensional and unsharpness measurements, is carried out on an artificial 3D phantom and on the CT scans of articles with the features of known dimensions. The capability of the method, with the special radiograph acquisition implemented into Shimadzu inspeXio SMX-225CT FPD HR industrial microfocus X-ray CT system, is also demonstrated on the detection of complex structural damage due to low-velocity impact, including accurate detection of through-the-thickness features, in large and thin composite laminate panels.

FIGS. 2A-2F are simplified schematics of a top view of a CT system 200 showing steps of a variable zoom acquisition trajectory including both rotation and translation of a specimen 202 for implementing the several embodiments of the disclosure. The CT system 200 includes an X-ray source 204 and an X-ray detector 206. The source 204 may emit a conical X-ray beam and project the specimen 202 within a field of view (FOV) 208 on the detector 206. The X-ray beam of the source 204 may be a collimated cone X-ray beam (e.g., 30-degrees wide). In an example, the source 204 has a 225 kV X-ray tube with a focal spot size of 4 µm. Other X-ray sources are contemplated by this disclosure. In an example, the detector 206 may be a 16-bit (65,536 intensity values) flat panel detector made of a cesium iodine (CsI) scintillator material and has an operational size of 417 mm. The detector 206 can be used in two acquisition modes: Fast (1000 by 1000 pixels, 0.417 mm pixel size) and Fine (3000 by 3000 pixels, 0.139 mm pixel size). Other X-ray detectors are contemplated by this disclosure. In an example, the X-ray source-to-detector distance (SDD) may be 800 mm, and scans were accomplished at 1 frame per second with 3 frames averaged. Other SSD, frame rates, and set sizes of averaged frames are contemplated by this disclosure. In various examples, the CT system 200 is implemented with the Shimadzu InspeXio SMX-225CT FPD HR industrial micro-CT system. The Shimadzu CT system hardware is capable of using non-conventional scanning trajectory. Shimadzu scanning software was modified to accept custom definition of an object trajectory, i.e. location of the rotation center at each rotation angle, and provided the reconstruction software with calibrated detector offsets at each location. Scanning parameters for pre-impregnated continuous fiber-reinforced polymer composite panels which have been subjected to low-velocity impact damage are outlined in Table 1.

TABLE 1

CT-scan parameters for the Carbon/Epoxy panel and hybrid composite panel

| | 401-mm Carbon/Epoxy panel | | 150-mm hybrid composite panel | |
|---|---|---|---|---|
| | Conventional method | Variable zoom method | Conventional method | Variable zoom method |
| Tube voltage, kV | 180 | 180 | 220 | 220 |
| Target current, µA | 90 | 90 | 70 | 70 |
| Magnification | 3x | 3x-10x | 8x | 8x-20x |
| Optimal voxel size, mm | 0.046 | 0.014 | 0.052 | 0.021 |
| Angular range, deg | 360 | 210 | 360 | 360 |
| Number of projections | 720 | 720 | 1200 | 1200 |
| Detector pixel size, mm | 0.139 | 0.139 | 0.417 | 0.417 |

The CT system 200 also includes a specimen stage (not shown) configured to securely position a region of interest (ROI) 210 of the specimen 202 within the FOV 208. The specimen stage both rotates the specimen 202 about a rotational axis and translates the specimen 202 within the FOV 208 along an acquisition trajectory between the source 204 and the detector 206. In various implementations, the acquisition trajectory maintains the rotational axis in a center of the FOV 208. In some implementation, the acquisition trajectory may move the rotational axis through other areas of the FOV 208. Therefore, the ROI 210 remains projected onto a central area of the detector 206 while the specimen 202 is translated between the source 204 and the detector 206. In some implementations, the ROI 210 may be projected onto a non-central area of the detector 206. The specimen stage may comprise a clamp for releasably affixing the specimen 202 to the specimen stage. The clamp is positioned on the specimen stage such that a central axis of the clamp is parallel to and coincident with the rotational axis of the specimen stage. The specimen 202 is affixed to the clamp at the ROI 210.

Figure 2A:
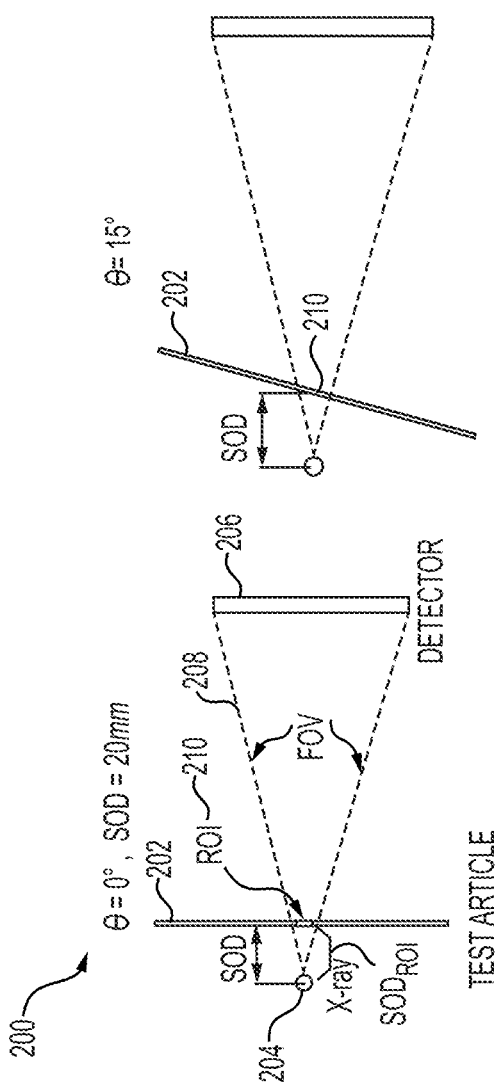
FIGS. 2A-2F are simplified schematics of a top view of a CT system showing steps of an acquisition trajectory including both rotation and translation of test article for implementing the several embodiments of the disclosure.
Figure 2B:
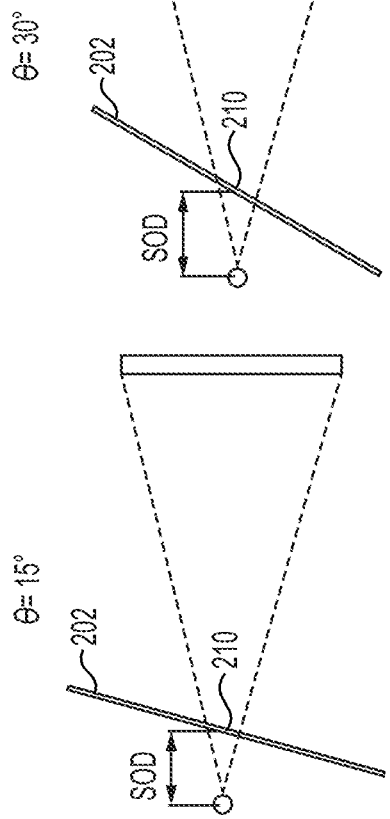
Figure 2C:
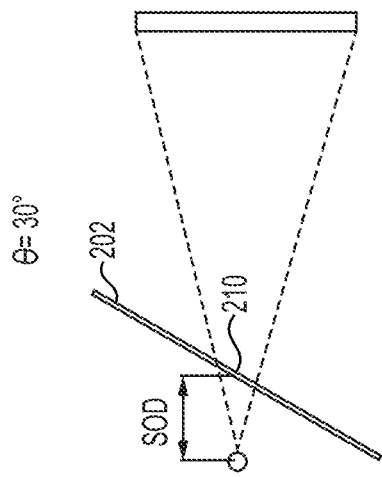
Figure 2D:
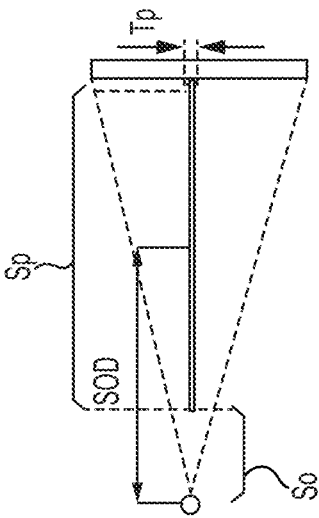
Figure 2E:
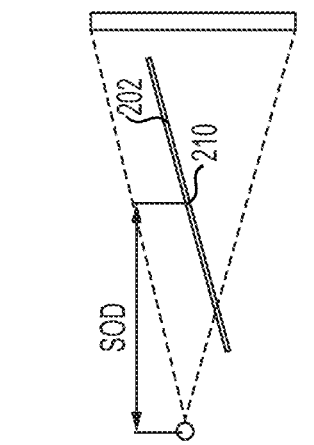
Figure 2F:
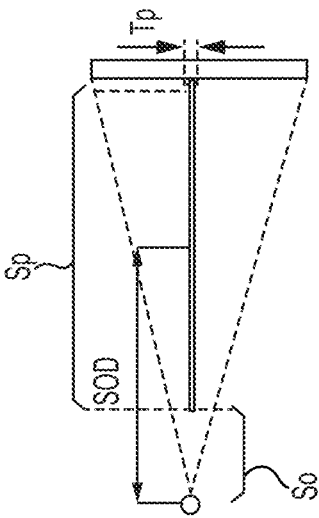

A controller (not shown) of the CT system 200 controls rotational and translational motion of the specimen stage during a scan of the specimen 202 and reconstructs the captured specimen using calibrated detector offsets at each location along the acquisition trajectory. The translational motion, or acquisition trajectory, of the specimen stage specifies a location (e.g., a distance from the source 204 along a center of the FOV 208) of the rotational axis of the specimen stage at each rotation angle. The distance from the source 204 to the rotational axis of the specimen stage, also known as source-to-object distance (SOD), is used for estimation of the maximum magnification factor and, as a result, the optimal spatial resolution. As the specimen rotates during the CT scan, it also translates according to a sinusoidal path:

$$SOD(\theta) = \max\{SOD_{ROI}, S_0 + \tfrac{1}{2}(T_p + (S_p - T_p)|\sin \theta|)\} \quad \text{Equation 1,}$$

where $SOD_{ROI}$ corresponds to a closest SOD at which the ROI is fully visible in the detector FOV 208, $S_0$ is a safety offset, $S_P$ is a specimen width, and $T_P$ is a specimen thickness. The $SOD_{ROI}$ also corresponds to a location at which a maximum magnification factor is achieved for the ROI. As shown in FIG. 2A, the specimen 202 is installed on the specimen stage via the clamp such that the ROI 210 is fully captured in the detector FOV 208. This position corresponds to the highest magnification at $\theta=0°$, as illustrated in the top view of the CT system 200 in FIG. 2A. The acquisition trajectory is selected to avoid collision of the specimen 202 with the source 204. For example, different values of $S_0$ may be selected for different specimens 202. In the examples shown in FIGS. 2A-2F, $SOD(\theta)=SOD_{ROI}$ for $|\theta|<15°$ and $SOD_{ROI}$ is selected to ensure that the ROI 210 remains in the FOV 208 for $|\theta|<15°$. Outside of the $|\theta|<15°$ range, the specimen 202 translates such that $SOD(\theta)$ is greater than $SOD_{ROI}$ and increases as $\theta$ increases according to the sinusoidal path in Eq. (1) until the $SOD(\theta)$ reaches a maximum SOD at $\theta=90°$. For example, FIGS. 2B-2F show how the SOD increases at each of $\theta=15°$, 30°, 45°, 75°, and 90°, respectively. While FIGS. 2B-2F only show the motion of the specimen 202 along the acquisition trajectory between 0° through 90°, the remainder of the acquisition trajectory may be readily understood through 360° due to symmetry. While described above with the example where the specimen stage translates and rotates while the source 204 and the detector 206 remain stationary, in some implementations, the source 204 and/or the detector 206 may additionally move during operation.

Figure 3:
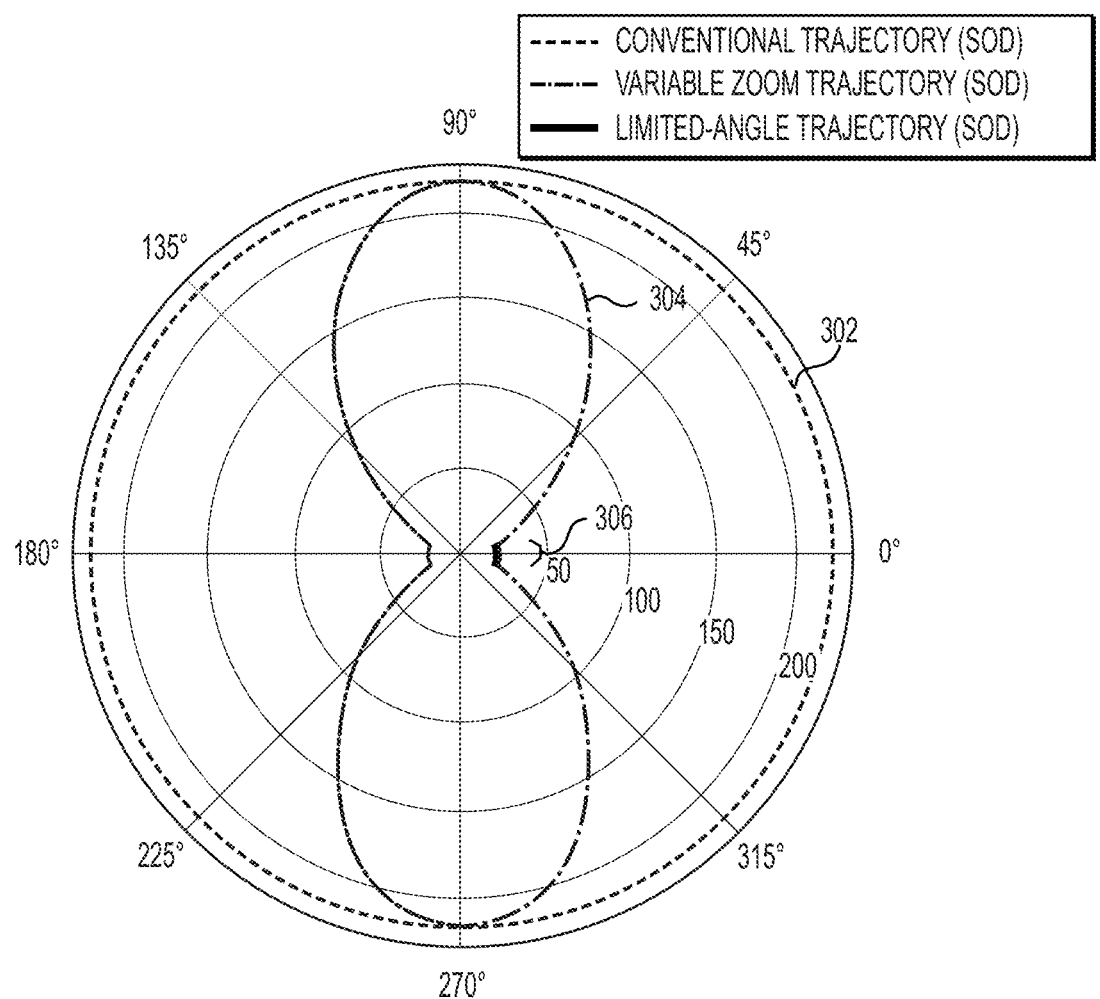
FIG. 3 is a radial diagram of the source-to-object distance (SOD) for conventional, variable zoom, and limited angle scanning trajectories.

FIG. 3 is a radial diagram of schematic trajectories of the SOD for conventional, variable zoom, and limited angle scanning trajectories. The radial coordinates correspond to the SOD, whereas the angular coordinates define angles of the scanning orbit (e.g., angles of the specimen stage). The SOD for the conventional trajectory remains constant during scanning as indicated by a first line 302. On the other hand, the SOD for the variable zoom acquisition trajectory varies according to the sinusoidal path as defined in Eq. 1. and is shown by a "peanut" shaped second line 304.

In the example shown in FIG. 3, the schematic trajectories are provided for a specimen width of 401 mm and negligible thickness and offset. In an example, a minimum distance necessary to capture a desired ROI in the detector FOV within $|\theta|<15°$ is $SOD_{ROI}=81$ mm. The SOD for conventional CT geometry is 265 mm since the specimen has to rotate 360° without hitting the source 204, while also maintaining the safety offset $S_0$ from the source 204. The SOD ($\theta$) for the variable zoom trajectory varies in the 81-265 mm range. The limited angle tomography (LAT) scan trajectory, which is also used for comparison, spans 30° at $SOD(\theta)=SOD_{ROI}$ for $|\theta|<15°$—a subset of the variable zoom trajectory, as shown by a bold third line 306. The reason for such small LAT angular range is that it is the largest angular span that can be achieved for the selected maximum magnification such that the test article does not interfere with the X-ray source.

In an example, the Shimadzu microfocus X-ray CT cabinet system inspeXio SMX-225CT FPD HR is utilized for all X-ray CT scans. It has a 225 kV X-ray tube with a capability to reach 4 µm focal spot size. The system uses high-resolution 16-bit flat panel X-ray detector, 417×417 mm in size, that can acquire up to 3000×3000-pixel radiographs. Distance from the X-ray tube to the flat panel detector, SDD, was set to 800 mm.

Reconstruction Method

Reconstruction of a three-dimensional (3D) volume from X-ray cone-beam projection radiographs represents a photon transmission tomography problem that has been extensively studied since 1970s. A historical review of the research in the field can be found in [12]. An analytical reconstruction method developed for the variable zoom scan trajectory disclosed herein is related to the industry-standard Feldkamp-Davis-Kress (FDK) algorithm [30], the disclosure of which is hereby incorporated by reference in its entirety. Analytical reconstruction methods are superior in terms of performance and are used in the majority of commercial medical or industrial X-ray CT systems.

The algorithm described in this section follows the presentation of filtered backprojection as convolution-backprojection method provided in reference [31]. In a first step, X-ray radiographs $P(x, y)$ are weighted to account for different ray lengths in a cone beam, defined as $P'_\theta(x, y_k)$, and convolved with a ramp filter. Pixel coordinates are assumed to be scaled to the center of rotation, i.e. their coordinates $(x, y_k)$ are divided by the magnification factor.

$$S_\theta(x, y_k) = \left[ \frac{P_\theta(x, y_k)}{\sqrt{1 + (x^2 + y_k^2)/SOD^2(\theta)}} * h(x) \right] \qquad \text{Equation (1)}$$

A step in this reconstruction algorithm is filtering of projections in the frequency domain. In the FDK algorithm a 1D filtering is applied to each row of a weighted 2D radiograph $P'_\theta(x, y_k)$ taken at angle $\theta$. In this work we use the following discrete spatial sampling of the ramp filter [31]:

$$h[np_x] = \frac{1}{(2p_x)^2} \begin{cases} 1, & n = 0 \\ 0, & n \text{ even} \\ -1/(\pi n/2)^2, & n \text{ odd} \end{cases} \qquad \text{Equation (2)}$$

where n is integer $n \in [-n_x^{zp}, n_x^{zp})$, $p_x$ is a row pixel spacing, $n_x^{zp}=(2n_x-1)_2$ rounded to the next power of two, and $n_x$ is the number of pixels in a projection row. The spatial convolution in Eq. 2 is implemented in the frequency domain as follows [31]:

$$[P'_\theta(x,y_k)*h(x)]=p_x\text{IFFT}\{\text{FFT}P'_\theta(x,y_k)_{zp} \cdot \text{FFT}h[np_x]_{shift}\} \qquad \text{Equation (3)}$$

where FFT/IFFT represent 1D direct and inverse discrete Fourier transform for real input, half-spaces of the filter $h[np_x]$ are swapped using fftshift method [32]; and radiographs are zero-padded to $n_x^{zp}$ indicated by subscript zp to avoid inter-period artefacts [31].

In the final step, backprojection of a set of filtered radiographs is performed over all projection angles with the additional weighting by $w^{vz}$:

$$v(t, s, r) = \sum_\theta w^{vz}(\theta) z_d^2(\theta) S_\theta(xz_d, yz_d), \qquad \text{Equation (4)}$$

where $$z_d(\theta) = \frac{1}{1 - z/SOD(\theta)},$$

$$(x, y, z)^T = R(\theta) R_V \cdot (t, s, r)^T$$

Here $v(t, s, r)$ represents reconstruction volume, $R_V$ in the volume transformation matrix and $R_\theta$ is the matrix of specimen rotation. Note that due to the variable zoom method acquisition trajectory, the "projection" coordinates $(x, y, z)$ are different for each projection angle according to varying $SOD(\theta)$. The following weighting factor was experimentally found to significantly improve quality of reconstructed through-the-thickness sections:

$$w^{vz}(\theta) = \frac{SOD(\theta)}{SDD} \qquad \text{Equation (5)}$$

Note that using this weighting factor corresponds to dividing the row pixel spacing $p_x$ in Eqs. (3-4) by the varying magnification factor in Eq. (6).

Variable magnification presents another reconstruction difficulty absent in conventional CT reconstructions. Reconstruction of a larger volume than the initial ROI, which is only partially visible in the detector, leads to artefacts that correspond to changing effective size of projections. The artefacts are due to the assumption of data periodicity by the Discrete Fourier transform. To eliminate these artifacts we apply periodic-smooth decomposition [33] to weighted radiographs and use the periodic part of the radiograph boundary for filtering.

To avoid artifacts at high resolution, reconstruction algorithm must accurately calculate backprojection contributions to voxels over any ray through the object. Discrete application of Eq. (5) involves interpolation of density values from the detector grid to the rotated volume grid. It turns out that "naïve" methods based on the interpolation of projection values or volume coordinates lead to low quality reconstructions. In this work we have implemented two interpolation methods developed specifically for tomographic reconstruction: Distance-driven method [34] and Separable Footprints method [35]. Both methods result in similar results for the presented test cases, the disclosures of which are hereby incorporated by reference in their entirety.

The following describes high-level steps in the implementation of the algorithm:
1. Calculate ramp filter in the frequency domain FFTh $[np_x]_{shift}$ according to Eq. (3);
2. Calculate projection/volume transformation $R(\theta)R_V$ for each projection angle/SOD;
3. Calculate weighted and filtered radiograph $S_\theta(x, y_k)$ using Eqs. (2, 4) and applying periodic-smooth decomposition [33] (on a graphics card).
4. Transform volume coordinates using $R(\theta)R_V$ transformation (on the graphics card);
5. Add backprojected pixel values to all voxels as shown in Eq. (5) and using an interpolation method [34-35] (on the graphics card).
6. Repeat starting from Step 2 for all projection angles/SOD.

Reconstruction of manufacturing irregularities or structural damage in composite structures typically requires high resolution volumes with at least hundreds, and preferably thousands of points in each dimension. In the algorithm described above, backprojection is by far the most time-consuming operation during the reconstruction; and its efficient implementation for large volumes must be based on highly parallel computing. In this work we use standard implementation of FFT and IFFT available in modern graphics card hardware and custom backprojection implementation of Eq. (5) that takes advantage of vector processing by implementing complex but identical interpolation calculations required for each volume point. In addition to per-voxel parallelization, graphics card processors offer multiple command streams that allow concurrent execution of vectorized calculations and memory transfers.

In various examples, a high performance reconstruction desktop computer is provided with the CT system 200 (e.g., Shimadzu InspeXio SMX-225CT FPT HD system) [29], the disclosure of which is hereby incorporated by reference in its entirety. In an example, the reconstruction computer has a dual 2.3 GHz Intel Xeon E5-2650v3 processor and NVIDIA Quadro M5000 graphics card with 2048 CUDA cores. As an example of computational performance, the reconstruction algorithm disclosed above accomplished reconstruction of 1329×1266×432 voxel volume (about 0.7 billion variables) using 820 2000×2000 pixel radiographs (about 3.3 billion equations) in less than 7 minutes. In this case, the radiographs were cropped to 2000×2000 pixels to reduce the amount of projection data to the size necessary for reconstruction.

With reference to the pre-impregnated continuous fiber-reinforced polymer composite panels described in Table 1 above, each panel has a distinct material system typically encountered in the aerospace applications. The first panel is an IMT-Carbon/8552-Epoxy composite laminate; and the second panel is a hybrid IMT-Carbon and S2-Glass/913-Epoxy composite laminate. Both panels were manufactured by Boeing using the prepregger (Hexcel) specifications [27-28].

To evaluate performance of the variable zoom technique, for both material systems, we compare it with the reconstructions based on a) limited-angle (30°) CT at the magnification defined by the size of the damaged area; and b) conventional full-angle CT at the magnifications defined by the size of the panel. The 30° angular span is selected to demonstrate capability of conventional limited-angle scan at best resolution.

Figure 4:
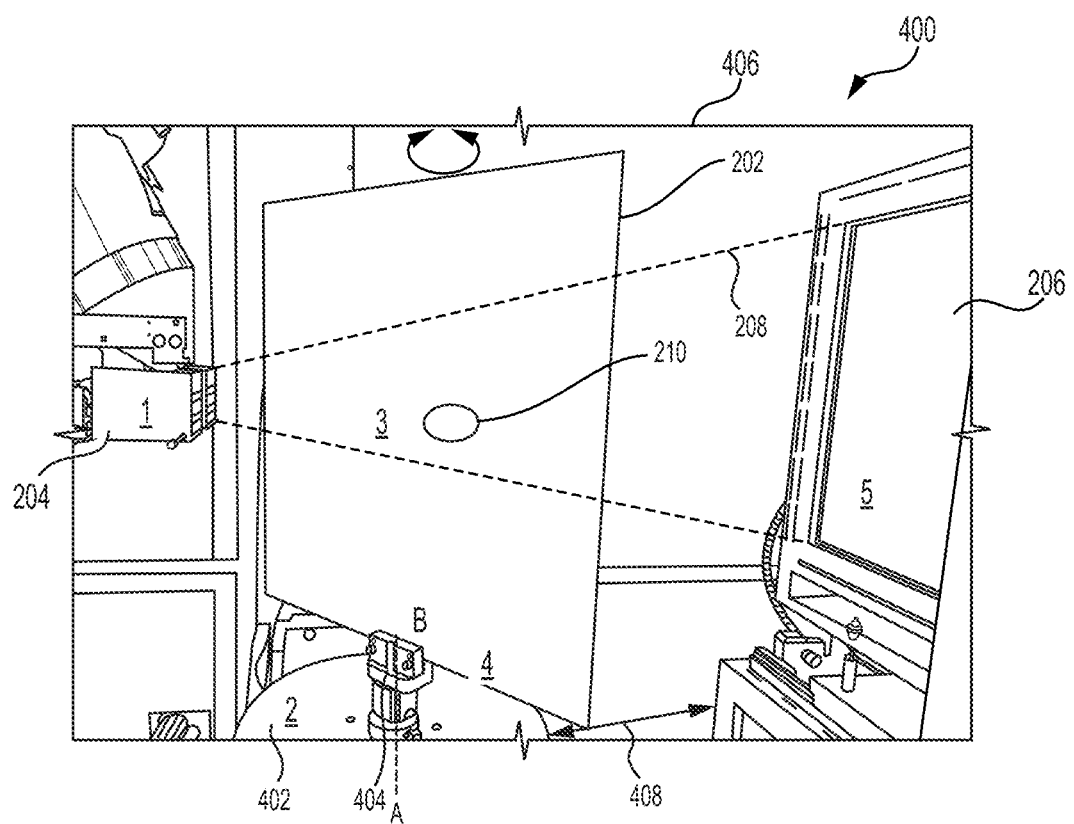
FIG. 4 is a system diagram of a variable zoom CT system.

FIG. 4 is a system diagram of a variable zoom CT system 400. The CT system 400 is substantially to the CT system 200 described above, with like numbers representing like parts. For example, the specimen 202, source 204, detector 206, and ROI 210 are substantially the same as described above. As described above, the source 204 is configured to emit an X-ray beam along the FOV 208 to the detector 206. The CT system 400 also includes a specimen stage 402, which is substantially the same as the specimen stage described above with reference to the CT system 200. Specifically, the specimen stage 402 both rotates the specimen 202 about a rotational axis A and translates the specimen 202 within the FOV 208 along an acquisition trajectory 408 between the source 204 and the detector 206. In the example show, the specimen stage 202 is rotated at 45°. The specimen stage 402 ay comprise a clamp 404 for releasably affixing the specimen 202 to the specimen stage 402. The clamp is positioned on the specimen stage such that a central axis B of the clamp 404 is parallel to and coincident with the rotational axis A of the specimen stage 402. The CT system 400 includes a housing 406 that encompasses the other components of the CT system 400. In various implementations, the housing 406 may provide radiation shielding to prevent radiation from the source 204 from entering a surrounding environment.

In the example shown in FIG. 4, the specimen 202 is a pre-impregnated continuous fiber-reinforced polymer composite (prepreg) panel which have been subjected to a low-velocity impact damage. For example, the specimen may be a 401-mm Carbon/Epoxy composite laminate panel. The panel contains impact damage, which is localized in the central part of the laminate.

Panel specimens represent a challenge for the conventional X-ray CT due to a large width-to-thickness aspect ratio. Large size of the panels prevent conventional CT scanning techniques from obtaining desired spatial resolution in the area susceptible to damage, which typically has the size comparable to panel thickness. Reliable defection of interlaminar defects requires reconstruction voxel size to be a few orders of magnitude smaller than the panel thickness. The variable zoom technique disclosed herein is compared with the reconstructions based on conventional full-angle CT at the minimum magnification dictated by the size of the panels; and limited angle CT at the maximum magnification. The variable zoom technique employs an acquisition trajectory with a variable SOD to obtain high-resolution CT scans. The trajectory proposed in this work acquires radiographs with higher geometric magnification by moving the inspected object closer to the X-ray source.

Composite panels under investigation present multiple distinct material systems. In an example, a first panel is an IMT-Carbon/8552-Epoxy laminate; whereas a second panel is a hybrid IMT-Carbon and S2-Glass/913-Epoxy composite laminate. Both panels were manufactured by Boeing using the prepregger (Hexcel) specifications [27-28]. For both material systems, the comparison of CT reconstructions is carried out for 1) conventional CT acquisition trajectory using the reconstruction software provided with the InspeXio SMX-225CT FPD HR system; 2) variable zoom acquisition trajectory disclosed herein; and 3) limited angle acquisition, both using the reconstruction algorithm described above. Line profile measurements across the defect boundary in Carbon/Epoxy composite laminate are used to confirm superior resolution of the variable zoom technique disclosed herein.

Carbon/Epoxy Composite Laminate Panel

A first example demonstrates the variable zoom technique for the inspection of the impact-damaged area in the Carbon/Epoxy panel. The width and thickness of the panel are 401 mm and 3.5 mm, respectively, resulting in width-to-thickness aspect ratio of 114.57. Impact damage is localized in a small 4×4.5 mm² area ROI 210 as illustrated in FIG. 4.

Figure 5:
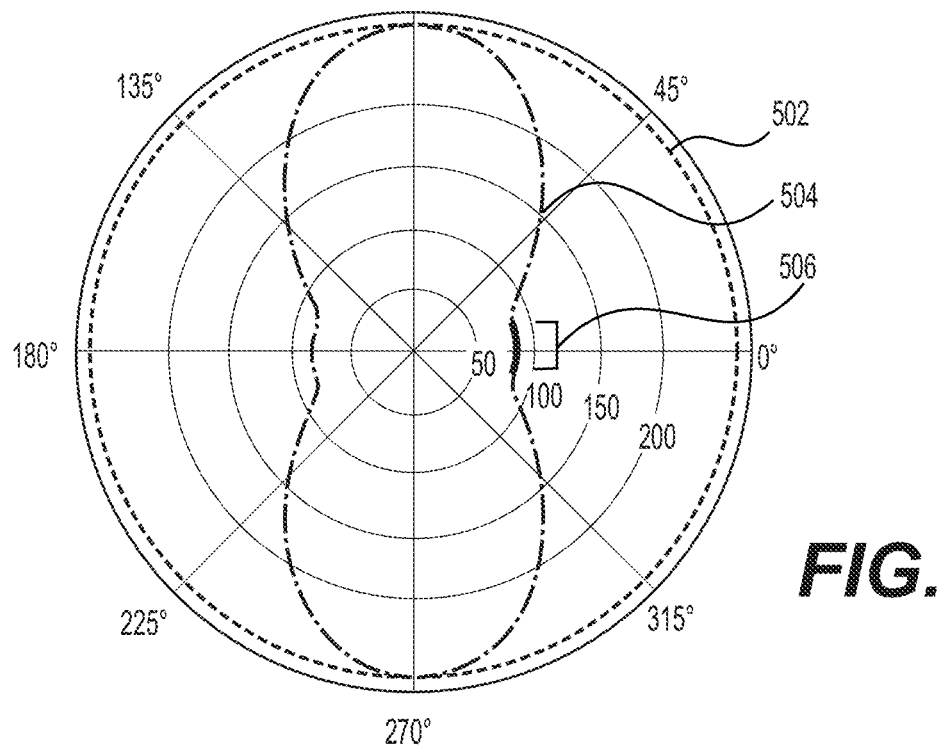
FIG. 5 is a radial diagram of the SOD for conventional, variable zoom, and limited angle scanning trajectories according to a first example.

FIG. 5 is a radial diagram of schematic trajectories of the SOD for conventional, variable zoom, and limited angle scanning trajectories. In the case of conventional scanning trajectory, the SOD 502 remains constant and equals 265 mm. The SOD 504 for variable zoom trajectory varies from 81 mm to 265 mm using the sinusoidal path as described in Eq. (1).

Conventional scanning trajectory achieves a 3× magnification for the specimen 202 corresponding to the optimal spatial resolution of 43 µm. On the other hand, the variable zoom technique is performed such that ROI 210 of the specimen 202 is projected onto the detector 206 according to the trajectory outlined in Eq. (1). The variable zoom method achieves a maximum 10× magnification for the impacted area in the 401-mm Carbon/Epoxy specimen. The optimal spatial resolution, in this case, can be 14 µm.

The scanning parameters for the first example are listed in Table 1, above. In the first example, a 210° angular range (known as short scan) for the variable zoom technique was used to reduce the acquisition time. Using the orbit described in Eq. (1) in the angular range $\theta \in [-105°, 105°]$. In the range ±15° a fixed SOD of 81 mm was used. Limited-angle reconstruction was accomplished by extracting the trajectory in the angular range $\theta \in [-15°, 15°]$ at the highest magnification. The optimal reconstruction voxel size of 43 µm is used for conventional scanning method and 14 µm for the variable zoom and limited-angle scanning techniques.

Figure 6A:
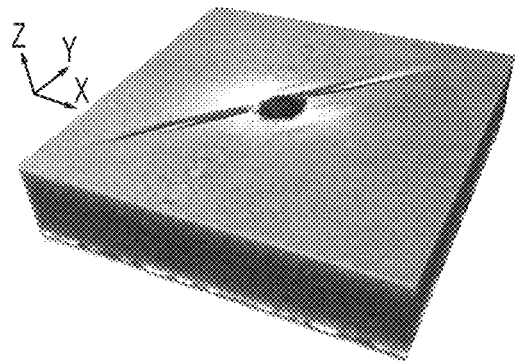
FIGS. 6A-6C are 3D reconstructed volumes of a Carbon/Epoxy panel for conventional, limited-angle, and variable zoom techniques, respectively.
Figure 6B:
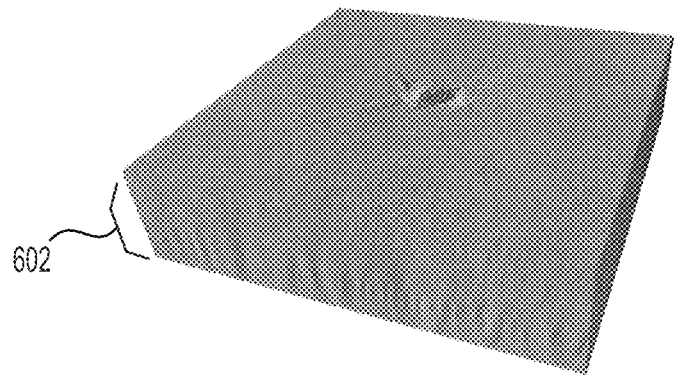
Figure 6C:
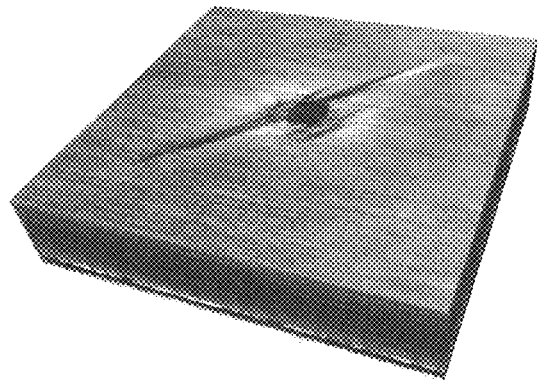

FIGS. 6A-6C illustrate the 3D reconstructed volumes of the Carbon/Epoxy panel obtained by the three scanning trajectories. Resolution and sharpness of the volume reconstructed with variable zoom technique is superior to the two others, although the three-dimensional view makes it difficult to distinguish individual features. Clearly, the limited-angle reconstruction does not allow discrimination of the microstructure of the damaged area. The conventional scan shown in FIG. 6A shows inadequate resolution. The limited-angle scan shown in FIG. 6B results in extremely shallow depth of field and incorrect results in the cross sectional planes, such as cross-sectional plane 602. The variable zoom technique shown in FIG. 6C produces adequate resolution in all three dimensions.

Figure 7C:
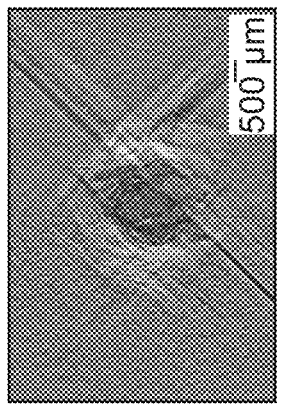
FIGS. 7A-7F are reconstructed slices in a through-thickness direction for the conventional scanning technique, the variable zoom technique, and the limited angle acquisition.
Figure 7F:
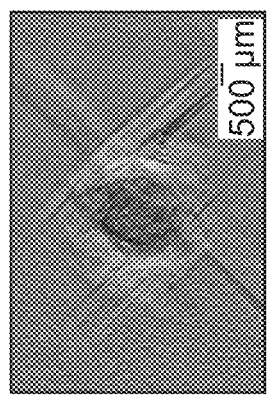
Figure 7B:
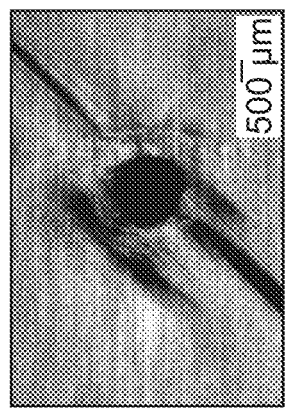
Figure 7E:
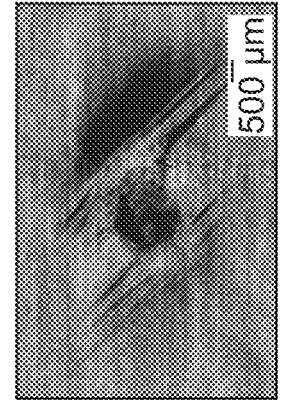
Figure 7A:
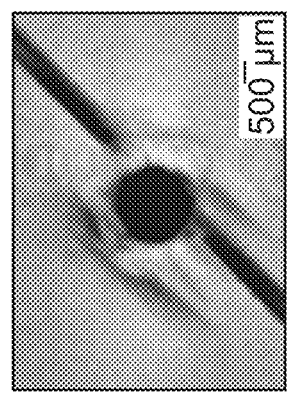
Figure 7D:
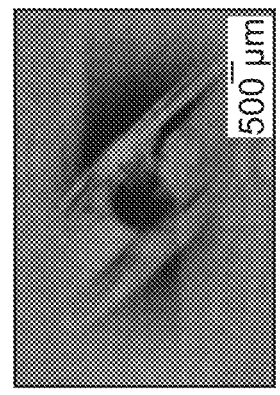

FIGS. 7A-7F are reconstructed slices in a through-thickness direction for the conventional scanning technique, the variable zoom technique, and the limited angle acquisition. Qualitative analysis of three-dimensional volumes can be carried out by examining slices at different through-thickness positions away from the damaged area as shown in FIGS. 7A-7F. For example, FIGS. 7A-C are reconstructed slices at a first through-thickness position for the conventional scanning technique, the variable zoom technique, and the limited angle acquisition, respectively. FIGS. 7D-7F are reconstructed slices at a second through-thickness position for the conventional scanning technique, the variable zoom technique, and the limited angle acquisition, respectively.

The conventional acquisition mode provides images which lack sharpness as shown in FIGS. 7A and 7D. Due to inadequate resolution, we cannot discriminate matrix damage of a small size. On the other hand, the variable zoom technique has a capacity to increase a spatial resolution. As a result, defects of a smaller size can be distinguished as shown in FIGS. 7B and 7E. Moreover, the images obtained using the variable zoom technique appear to have better sharpness as observed by visual inspection. The slices obtained by the limited-angle acquisition appear highly distorted in the through-the-thickness direction due to lack of projections, as shown in FIGS. 7C and 7F.

Figure 8C:
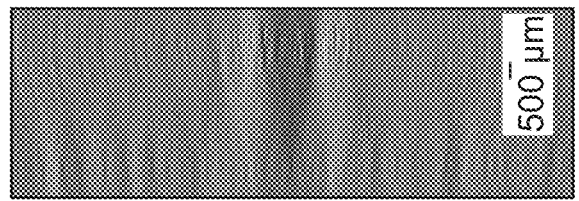
FIGS. 8A-8C are reconstructed slices in an across-the-thickness direction for conventional scanning, variable zoom, and limited angle techniques.
Figure 8B:
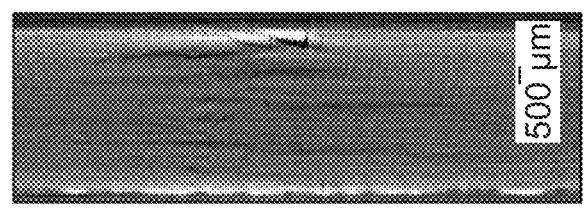
Figure 8A:
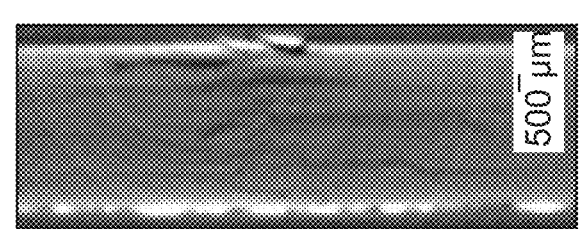

FIGS. 8A-8C are reconstructed slices in an across-the-thickness direction for conventional scanning, variable zoom, and limited angle techniques, respectively. The same trends discussed above with the slices of FIGS. 7A-7F emerges by inspecting slices along in the through-the-thickness direction, as shown in FIGS. 8A-8C. Note the improved through-the-thickness sharpness and clarity of delamination reconstruction shown in FIG. 8B by the variable zoom technique. As shown in the example of limited angle acquisition in FIG. 8C, the through-the-thickness resolution suffers most due to lack of angular data, leading to the detectable defects being smeared through the large thickness range for the 30° scan. The variable zoom acquisition trajectory defined in Eq. (1) was expected to improve the resolution of planar slices shown in FIGS. 7B and 7E, but unexpectedly, the variable zoom technique also improved the through-the-thickness slices shown in FIG. 8B. Clearly superior quality of the through-the-thickness slices obtained by the variable zoom technique is due to the novel weighting schema proposed in Eq. (6).

Hybrid Composite Laminate Panel

Figure 9:
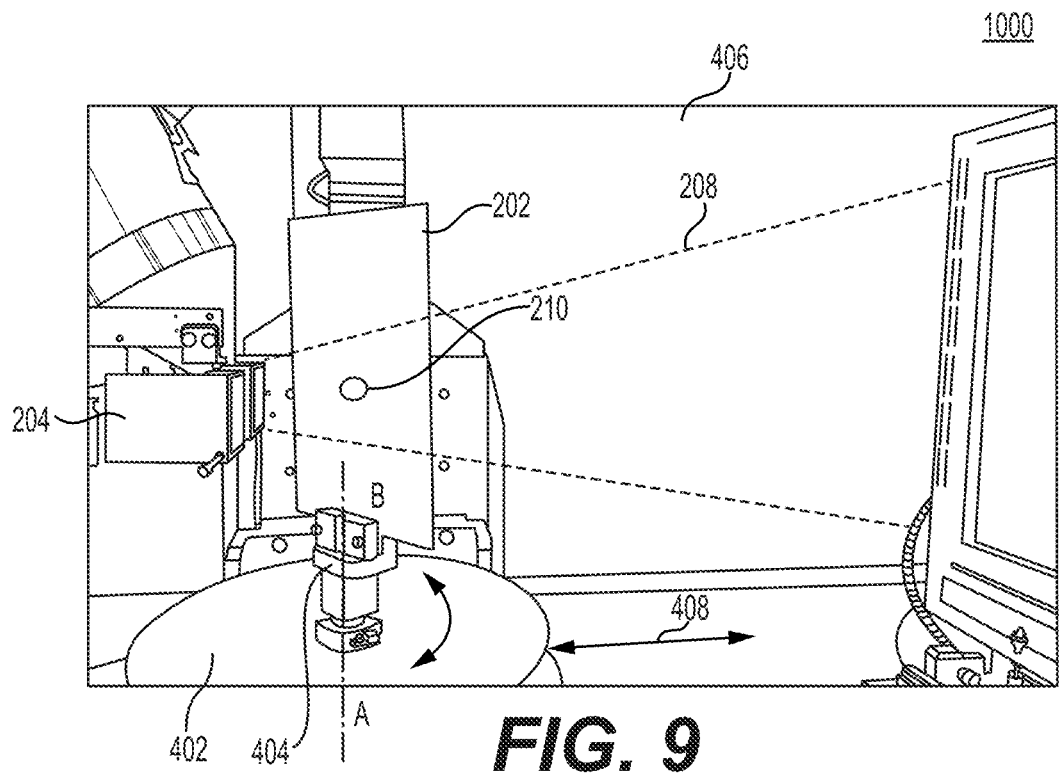
FIG. 9 is a system diagram of a variable zoom CT system.

In another example, the variable zoom technique is used to characterize a hybrid composite laminate panel. The hybrid composite laminate panel material system imposes additional challenge due to large contrast variation between Carbon and Glass fibers. FIG. 9 is a system diagram of a variable zoom CT system 900. The CT system 900 is substantially to the CT systems 200, 400 described above, with like numbers representing like parts. For example, the specimen 202, source 204, detector 206, and ROI 210 are substantially the same as described above. As described above, the source 204 is configured to emit an X-ray beam along the FOV 208 to the detector 206. The CT system 900 also includes a specimen stage 402, which is substantially the same as the specimen stage described above with reference to the CT system 200. Specifically, the specimen stage 402 both rotates the specimen 202 about a rotational axis A and translates the specimen 202 within the FOV 208 along an acquisition trajectory 408 between the source 204 and the detector 206. In the example show, the specimen stage 202 is rotated at 45°. The specimen stage 402 may comprise a clamp 404 for releasably affixing the specimen 202 to the specimen stage 402. The clamp is positioned on the specimen stage such that a central axis B of the clamp 404 is parallel to and coincident with the rotational axis A of the specimen stage 402. The CT system 900 includes a housing 406 that encompasses the other components of the CT system 900. In various implementations, the housing 406 may provide radiation shielding to prevent radiation from the source 204 from entering a surrounding environment.

In the example shown in FIG. 9, the specimen 202 is a hybrid composite laminate panel with a width of 152 mm and a thickness of 5.2 mm. The aspect ratio, in this case, is 29.23. An impact damage is located in the center of the specimen 202 at the ROI 210 and occupies approximately 3×3 mm² area as illustrated in FIG. 9.

Figure 10:
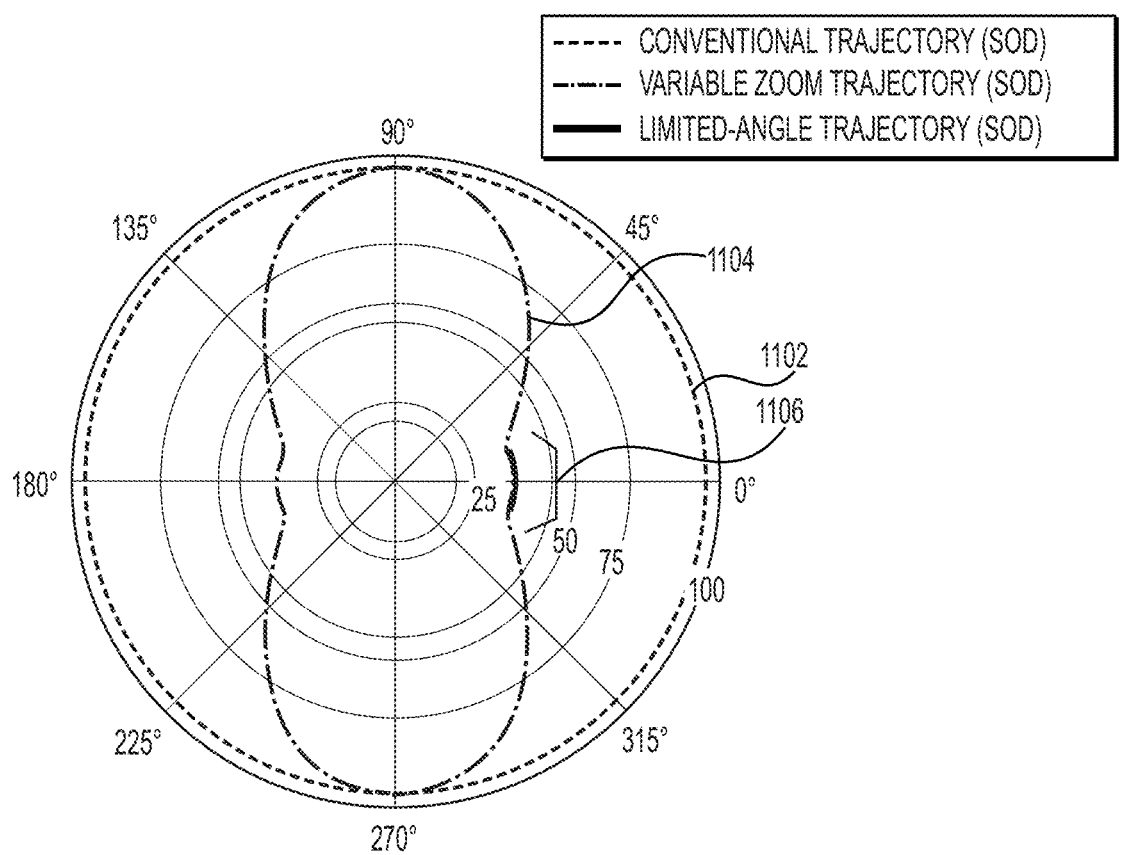
FIG. 10 is a radial diagram of schematic trajectories of the SOD for conventional, variable zoom, and limited angle scanning trajectories.

FIG. 10 is a radial diagram of schematic trajectories of the SOD for conventional, variable zoom, and limited angle scanning trajectories. Following the example of FIG. 9, the SOD 1002 for the conventional acquisition mode is 100 mm. The SOD 1004 for the variable zoom trajectory is in the range of 38 to 100 mm. Also presented are results for the limited-angle acquisition, again by extracting the radiographs that correspond to the angular range $\theta \in [-15°, 15°]$ at the maximum magnification with the SOD 1006.

The relatively low width-to-thickness aspect ratio of the panel allows achieving 8× magnification for conventional scanning. In contrast, the variable zoom technique was able to increase the magnification up to 20×. A summary of CT-scan parameters for the specimen 202 of FIG. 9 is provided in Table 1, above. It is important to note that in this example the variable zoom technique utilizes a 360° angular range in the course of scanning.

Figure 11A:
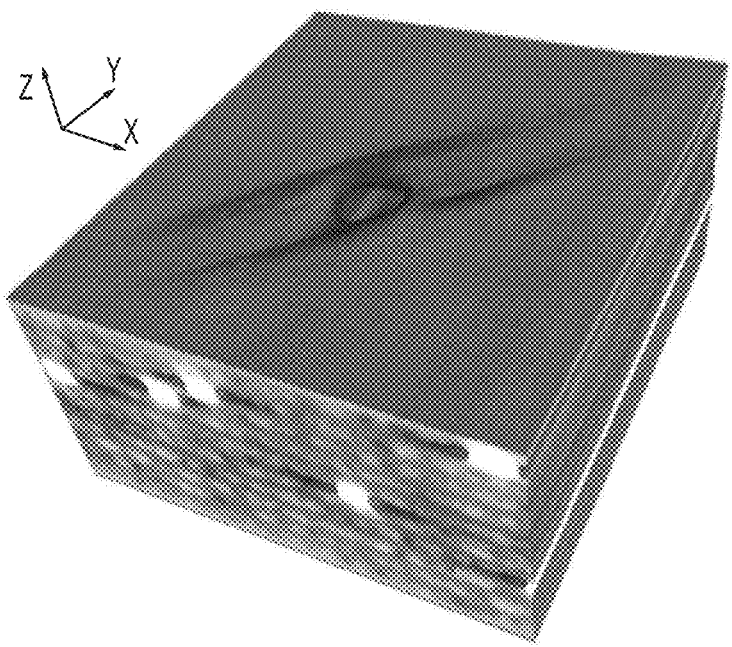
FIGS. 11A-11B illustrate the 3D reconstructed volumes of the hybrid composite laminate panel obtained by the conventional and variable zoom scanning trajectories.
Figure 11B:
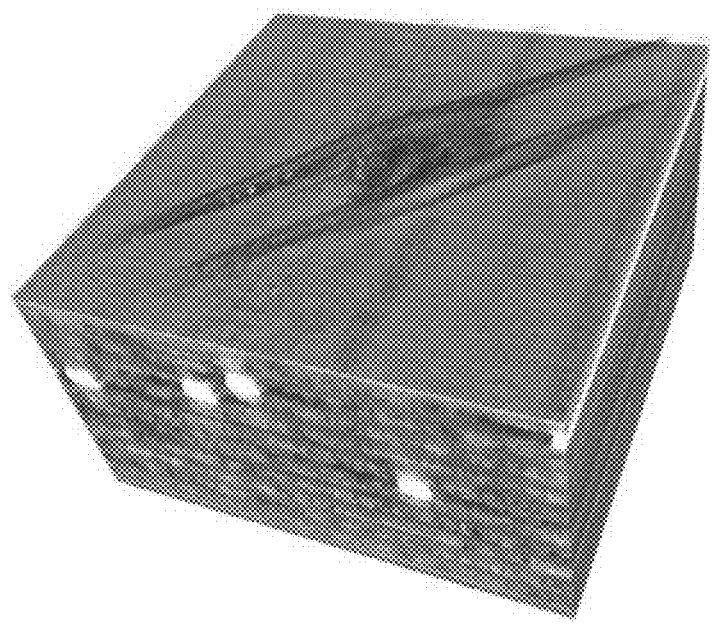

FIGS. 11A-11B illustrate the 3D reconstructed volumes of the hybrid composite laminate panel obtained by the conventional and variable zoom scanning trajectories. It can be observed that the reconstructed volume for the variable zoom technique shown in FIG. 11B has a superior quality as compared to the conventional scanning shown in FIG. 11A. Again, a clearly improved quality of the through-the-thickness reconstruction slices is not obviously expected and follows from the application of the projection weighting provided by Eq. (6).

Figure 12C:
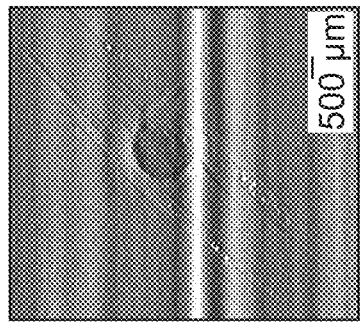
FIGS. 12A-12F are reconstructed slices in an across-the-thickness direction and a through-thickness direction for the conventional scanning technique, the variable zoom technique, and the limited angle acquisition.
Figure 12F:
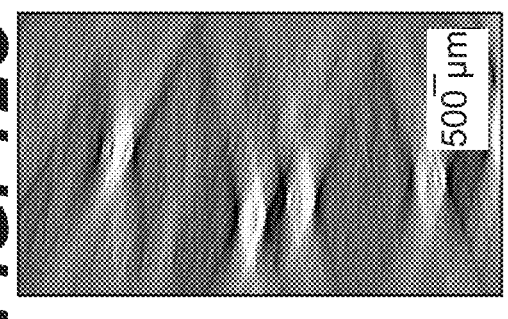
Figure 12B:
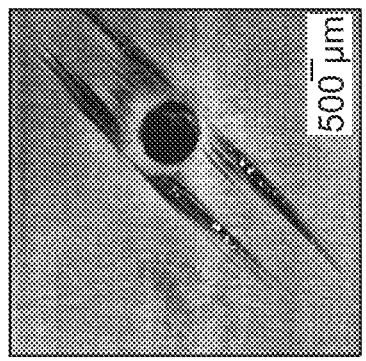
Figure 12E:
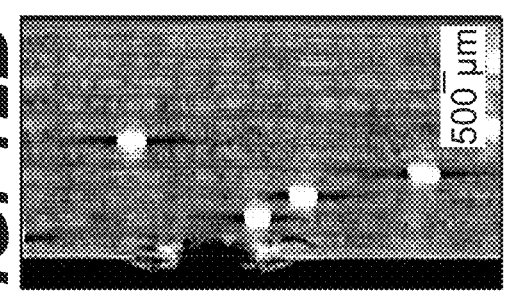
Figure 12A:
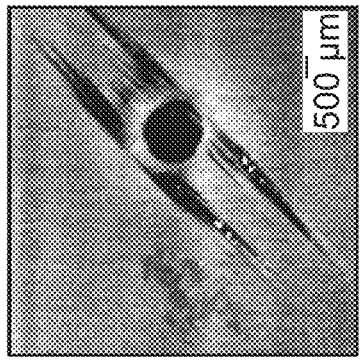
Figure 12D:
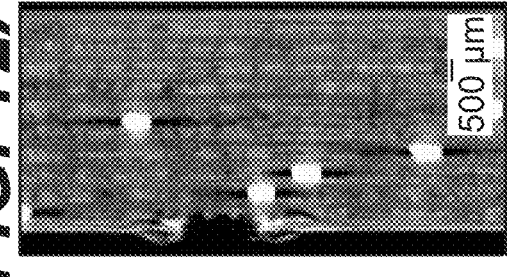

FIGS. 12A-12F are reconstructed slices in an across-the-thickness direction and a through-thickness direction for the conventional scanning technique, the variable zoom technique, and the limited angle acquisition. FIGS. 12A-12C show slices in the across-the-thickness direction for the conventional scanning technique, the variable zoom technique, and the limited angle acquisition, respectively. FIGS. 12D-12F show slices in the through-thickness direction for the conventional scanning technique, the variable zoom technique, and the limited angle acquisition, respectively. The reconstruction is conducted using a voxel size of 23 μm when projections are acquired by each of the methods under consideration. It is evident that images obtained by the variable zoom acquisition trajectory have a better sharpness as illustrated in FIGS. 12B & 12E. Despite the relatively high magnification factor which is utilized in a conventional acquisition mode, the spatial resolution appears to be inadequate to provide a desired reconstruction quality. On the other hand, the variable magnification in the course of scanning allows achieving higher spatial resolution; thus leading to a better reconstruction quality. In fact, all slices are susceptible to characteristic artifacts due to the presence of metal-coated fibers (X-ray tracers) detectable in a plain radiograph. These artifacts are more pronounced in the slices for limited-angle tomography and lead to deterioration of the imaging quality, as illustrated in FIGS. 12C & 12F.

FIGS. 13A-13D are reconstructed slices in a through-thickness direction and an across-the-thickness direction for the variable zoom using weighting and not using weighting. FIGS. 13A and 13B are reconstructed slices in a through-thickness direction and an across-the-thickness direction for the variable zoom using the weighting factor defined in Eq. (6). In comparison, FIGS. 13B and 13D are reconstructed slices in a through-thickness direction and an across-the-thickness direction for the variable zoom not using the weighting factor defined in Eq. (6). Although the reconstructed slice along the across-the-thickness direction show less noise in FIG. 13D, the reconstructed slice in the through-thickness direction in FIG. 13B shows large distortions of features in depth direction, which is most obviously demonstrated by the star patterns from the high-density tracers. FIG. 13D also shows distortion by the tracer obstruction in the section. In contrast, when using the weighting factor defined in Eq. (6), these distortions from the high-density tracers is not present in the reconstructed slices in FIGS. 13A and 13C.

Accuracy and Sharpness Measurements

Disclosed herein is a novel X-ray Computed Tomography method that is able to increase the spatial resolution for inspection of composite laminates with large in-plane dimensions. The novel scanning technique utilizes a non-conventional scanning trajectory, where the specimen not only rotates, but also translates towards the X-ray source as dimensions of the space allow; hence leading to a greater spatial resolution. The variable zoom method was demonstrated to outperform both conventional and limited-angle scanning methods. Unlike the conventional and limited-angle techniques, the variable zoom CT produced remarkable resolution in all three dimensions.

The approach incorporates two proposals: a nonconventional trajectory of radiograph acquisition and a novel reconstruction weighting scheme. The scanning trajectory includes simultaneous angular rotation and translation of a specimen towards the X-ray source as dimensions of the specimen permit; hence leading to a greater spatial resolution. Each radiograph is scaled by a weighting factor proportional to the distance from an object to the X-ray source. The variable zoom method was demonstrated to outperform both the conventional and the limited-angle scanning methods. Unlike the latter techniques, the variable zoom method produced remarkable resolution in all three dimensions.

To validate the proposed method, a feasibility study was performed on two composite laminate panels manufactured from different composite material systems and subjected to low-velocity impact loads. Both panels had relatively large thickness-to-width aspect ratio, which is a known challenge for a conventional CT scanning technique. In fact, conventional CT was not able to achieve the spatial resolution necessary to clearly differentiate smaller cracks and delaminations due to impact; while the limited angle tomography technique has shown complete lack of interlaminar defect resolution. Variable zoom CT was able to reconstruct volumes with higher spatial resolution hence leading to a better sharpness of reconstructed slices. Improved sharpness of the reconstruction by the variable zoom method was especially noticeable in through-the-thickness sections leading to significant improvement in the interlaminar defect detection. These results were consistent for both material systems under investigation. A quantitative analysis of measurement accuracy and sharpness of defect reconstruction was conducted on the machined defect of known geometry and dimensions. Variable zoom technique provided accurate in-plane and out-of-plane measurements of the defect dimensions as compared to measurements obtained by mechanical instruments; and a superior sharpness of reconstructed sections based not only on the visual inspection but also on the analysis of line profiles.

The variable zoom CT method developed in this work has significant implications for NDI of composite materials and structures. On the materials side, this method can address the need in achieving the maximum resolution of a CT system without destroying a test article by cutting a small section that can be placed close enough to the X-ray source for sufficient geometric magnification. There is a similar need for composite structures that can fit into existing CT system enclosures, but are subject to small flaws with critical features in three dimensions which are not recognizable using the conventional scanning techniques. Also, the new method offers additional flexibility towards enabling high-resolution CT for larger structures currently not suitable for microfocus CT systems.

It should be appreciated that the logical operations described herein with respect to the various figures may be implemented (1) as a sequence of computer implemented acts or program modules (i.e., software) running on a computing device (e.g., the computing device described in FIG. 14), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 14:
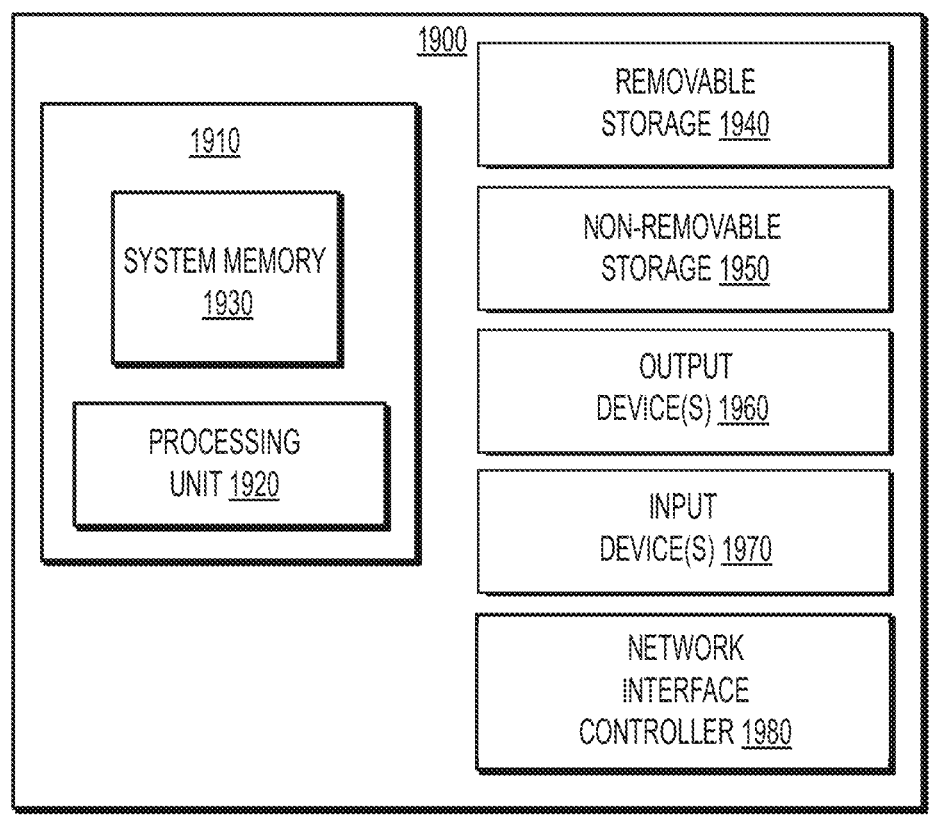
FIG. 14 illustrates an exemplary computer system suitable for implementing the several embodiments of the disclosure.

Referring to FIG. 14, an example computing device 1900 upon which embodiments of the invention may be implemented is illustrated. For example, the controller system described herein may each be implemented as a computing device, such as computing device 1900. It should be understood that the example computing device 1900 is only one example of a suitable computing environment upon which embodiments of the invention may be implemented. Optionally, the computing device 1900 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In an embodiment, the computing device 1900 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computing device 1900 to provide the functionality of a number of servers that is not directly bound to the number of computers in the computing device 1900. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In its most basic configuration, computing device 1900 typically includes at least one processing unit 1920 and system memory 1930. Depending on the exact configuration and type of computing device, system memory 1930 may be volatile (such as random access memory (RAM)), non-volatile (such as read-only memory (ROM), flash memory, etc.), or some combination of the two. This most basic configuration is illustrated in FIG. 14 by dashed line 1910. The processing unit 1920 may be a standard programmable processor that performs arithmetic and logic operations necessary for operation of the computing device 1900. While only one processing unit 1920 is shown, multiple processors may be present. Thus, while instructions may be discussed as executed by a processor, the instructions may be executed simultaneously, serially, or otherwise executed by one or multiple processors. The computing device 1900 may also include a bus or other communication mechanism for communicating information among various components of the computing device 1900.

Computing device 1900 may have additional features/functionality. For example, computing device 1900 may include additional storage such as removable storage 1940 and non-removable storage 1950 including, but not limited to, magnetic or optical disks or tapes. Computing device 1900 may also contain network connection(s) 1980 that allow the device to communicate with other devices such as over the communication pathways described herein. The network connection(s) 1980 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. Computing device 1900 may also have input device(s) 1970 such as a keyboards, keypads, switches, dials, mice, track balls, touch screens, voice recognizers, card readers, paper tape readers, or other well-known input devices. Output device(s) 1960 such as a printers, video monitors, liquid crystal displays (LCDs), touch screen displays, displays, speakers, etc. may also be included. The additional devices may be connected to the bus in order to facilitate communication of data among the components of the computing device 1900. All these devices are well known in the art and need not be discussed at length here.

The processing unit 1920 may be configured to execute program code encoded in tangible, computer-readable media. Tangible, computer-readable media refers to any media that is capable of providing data that causes the computing device 1900 (i.e., a machine) to operate in a particular fashion. Various computer-readable media may be utilized to provide instructions to the processing unit 1920 for execution. Example tangible, computer-readable media may include, but is not limited to, volatile media, non-volatile media, removable media and non-removable media implemented in any method or technology for storage of information such as computer readable instructions, data structures, program modules or other data. System memory 1930, removable storage 1940, and non-removable storage 1950 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

In an example implementation, the processing unit 1920 may execute program code stored in the system memory 1930. For example, the bus may carry data to the system memory 1930, from which the processing unit 1920 receives and executes instructions. The data received by the system memory 1930 may optionally be stored on the removable storage 1940 or the non-removable storage 1950 before or after execution by the processing unit 1920.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Embodiments of the methods and systems may be described herein with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Phantom-Based Evaluation of Variable Zoom Technique

Phantom Definition

In this section the performance of the Variable Zoom technique is assessed using an artificial 3D phantom. The phantom volume represents a rectangular 400 mm-wide and 3.5 mm-thick block with a cylindrical defect (0.5 mm in diameter and height) located in the center of the phantom. Dimensions of the phantom mimic the composite panels are presented below. The cone-beam projections of a phantom are generated using the projector function and using the geometric parameters and acquisition trajectories for the Carbon/Epoxy panel shown in FIG. 3. To avoid "inverse crime", projections of the phantom volume are generated using a voxel size that is smaller than the one in the projected volume. Due to memory limitations, the full volume is divided in two parts. A smaller inner part with a defect is projected with a 2 µm voxel size and the bigger outer part is generated with 10 µm voxel size. Resulting projections are combined and used as inputs for the reconstruction based on the algorithm described above in the Reconstruction Method section.

Measurements of Defect Sharpness

Visual inspection reveals substantial difference in the sharpness of Variable Zoom and conventional CT reconstruction slices. To assess this difference quantitatively, we adopted the variance estimation method proposed in Kraemer A, Kovacheva E, Lanza G, "Projection based evaluation of CT image quality in dimensional metrology," Digit. Ind. Radiol. Comput. Tomogr., 2015, p. 1-10. For each point on the defect boundary, variance of intensity values inside a support window indicates local sharpness of the material-defect boundary. The maximum variance among all measurements along the defect boundary is chosen to represent the sharpness.

Figure 15:
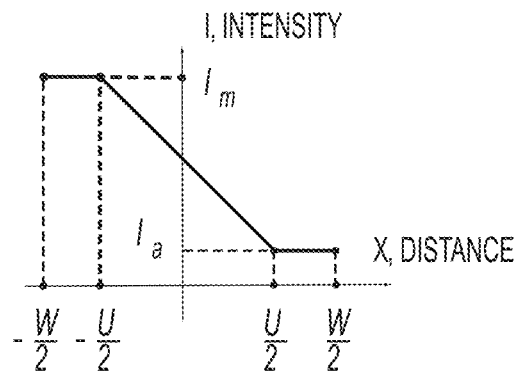
FIG. 15 shows normalized intensity profile across the boundary of a defect.

While ideal for complex boundaries, variance values are difficult to interpret and compare quantitatively. To mitigate this issue, we propose a relationship that estimates the unsharpness of a boundary based on the measured variance. A relationship is established for one-dimensional boundary such that the variance of intensity values along the line profile is related to apparent unsharpness. An assumed intensity profile of the length w across the boundary with unsharpness u is used to calculate the variance for the line profile as illustrated in FIG. 15. Here $I_m$ corresponds to material intensity and $I_a$ to defect/air intensity.

Intensity for the profile shown in FIG. 15 can expressed as a function of a profile coordinate:

$$I(x) = \begin{cases} I_m, x \in \left[-\frac{w}{2}, -\frac{u}{2}\right] \\ \frac{I_m + I_a}{2} - \frac{x(I_m - I_a)}{u}, x \in \left[-\frac{u}{2}, \frac{u}{2}\right] \\ I_a, x \in \left[\frac{u}{2}, \frac{w}{2}\right] \end{cases} \quad (7)$$

The variance of intensity for this profile can be calculated and further estimated as:

$$\text{Var} = \frac{1}{N}\sum_{k=1}^{N}(I_k - \bar{I})^2 \xrightarrow[N\to\infty]{} \frac{1}{w}\int_{-w/2}^{w/2}(I(x)-\bar{I})^2 dx, \quad (8)$$

where $I_k$ is the intensity of a pixel and $$\bar{I} = \frac{I_m + I_a}{2}$$

is the average intensity or the profile.

Substituting Eq. (7) in Eq. (8) and calculating the integral allows expressing the unsharpness u as a function of the variance:

$$u = 3/2w(1-\text{Var}_n), \quad (9)$$

where $$\text{Var}_n = \frac{4\,\text{Var}}{(I_m - I_a)^2}$$

is a normalized variance used in the plots below.

Figure 16:
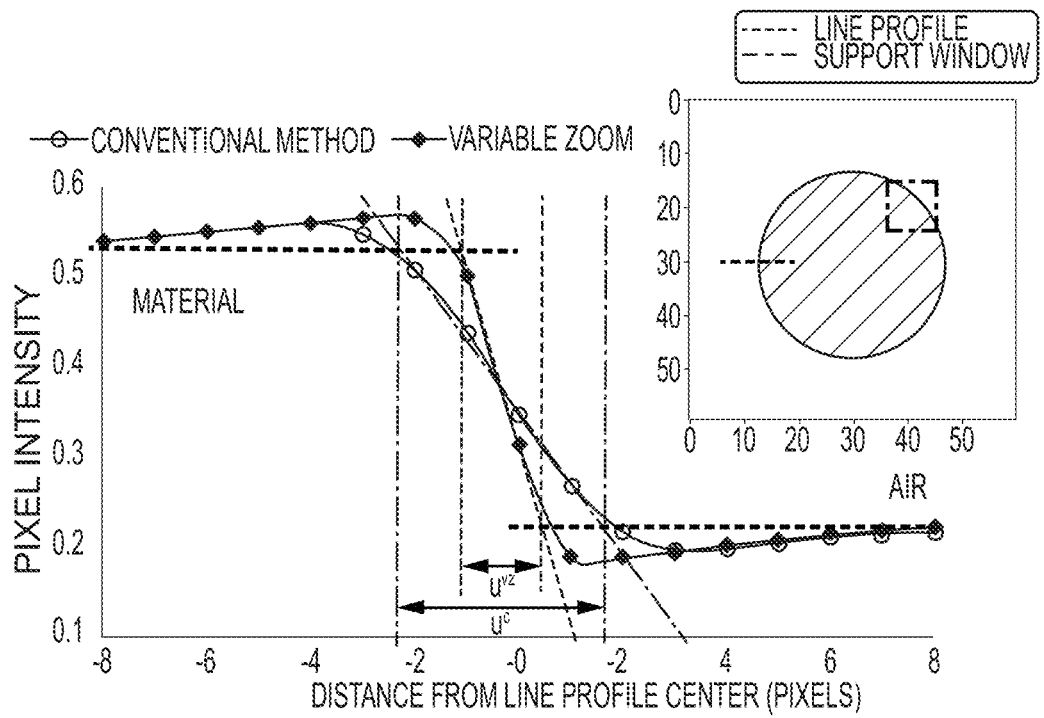
FIG. 16 shows an estimation of a boundary sharpness based on line profile.

FIG. 16 compares apparent unsharpness of a typical profile for the 500-μm cylindrical void in the 400-mm phantom for both reconstruction methods. A 16-pixel line profile is centered at a point on the material-air boundary defined above. Note that material/air intensities are averaged over large sections away from the boundary. Due to a reconstruction artifact that increases pixel intensity at the material side and decreases it at the air side, the apparent unsharpness is measured as a distance between the intersections of the slope line with the average material/air levels. FIG. 16 shows that the apparent unsharpness $u^{vz}$ for Variable Zoom is almost three times smaller than the unsharpness $u^c$ for the conventional method.

Figure 17:
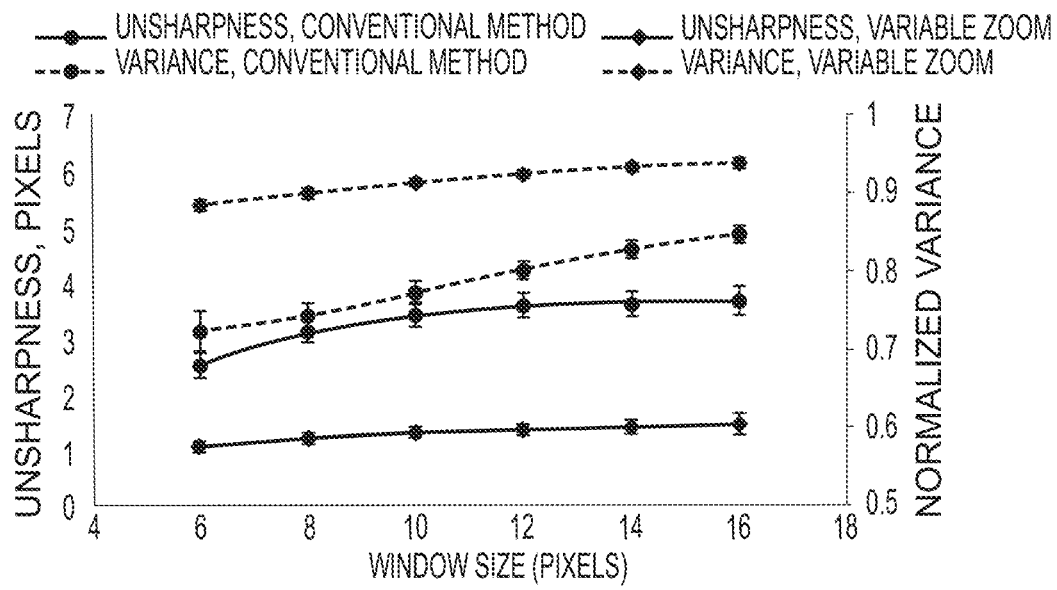
FIG. 17 shows phantom boundary unsharpness and normalized variance as function of window size.

FIG. 17 demonstrates the normalized variance calculated from a discrete form of Eq. (8) and the unsharpness from Eq. (9) as a function of window size. A w×w-pixel support window is used for each point on the contour of a hole to obtain maximum variance for the slice. Similar to FIG. 16, to avoid overestimation of the unsharpness due to the boundary artifact, intensity values in the window are clamped to the average material intensity from above and to average air intensity from below. This correction removes the effects of boundary artifacts so that the measured profiles follow the profile in FIG. 15 and Eq. (9) can be used for calculation of the unsharpness. Measurements were performed on 20 sections along the depth of the hole and the error bars indicate standard deviations. As expected, maximum normalized variance of a contour grows almost linearly with respect to window size, while the calculated boundary unsharpness stabilizes after growth at small window sizes. Comparison with FIG. 16 confirms the accuracy of estimating unsharpness based on variance as FIG. 17 shows similar ratio of the unsharpness values for the two methods. Additionally, note that for all windows sizes, the Variable Zoom technique consistently delivers superior sharpness of reconstruction as compared to the conventional method.

Measurement-Based Validation of Variable Zoom Technique

Dimensional Measurements in a Composite Panel

Measurement-based validation was carried out on a large aspect ratio Carbon/Epoxy composite panel shown in FIG. 4 manufactured by Boeing using the Hexcel prepreg. A 0.5-mm hole was drilled in the middle of the panel, and the hole's diameter was confirmed by the Keyence Digital Microscope VHX-950F. The depth of the defect was 2.5 mm, which was estimated by a dial test indicator with 0.001 in (25.4 μm) precision. The dimensional measurements as well as the unsharpness measurements were performed using the procedures outlined in the previous section.

CT scans of the panel were generated using 180 kV X-ray tube voltage, 90 μA target current, and 1 frame/sec acquisition speed. 720 3000×3000 radiographs were acquired in a 360-degree angular range. Magnification factor equals 3× for the conventional CT (46 μm optimal voxel size) and varies in 3×-10× range for the Variable Zoom technique.

Figure 18:
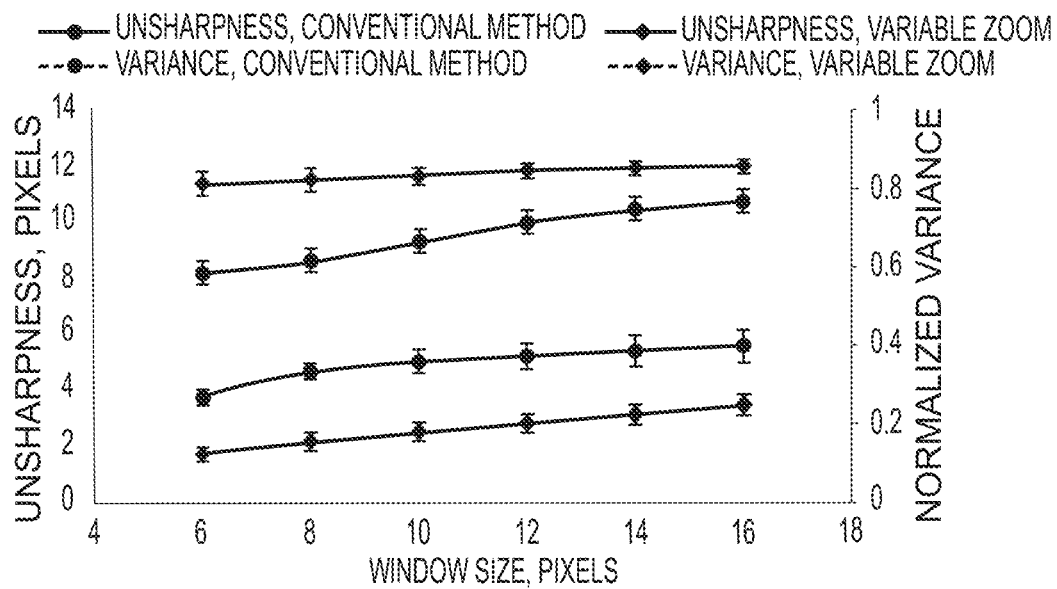
FIG. 18 shows drilled hole boundary unsharpness and normalized variance as a function of window size.

FIG. 18 provides the normalized variance measurements and unsharpness calculations for 20 sections of drilled hole in the Carbon/Epoxy composite panel. It is evident the Variable Zoom technique results in better sharpness than the conventional CT. Both methods exhibit higher unsharpness values as compared to phantom due to the presence of noise in the radiographs.

Application of Variable Zoom Technique to Composite Panels with Impact Damage

Test Specimens

The Variable Zoom technique is demonstrated on X-ray CT scans of pre-impregnated continuous fiber-reinforced polymer composite panels which have been subjected to low-velocity impact damage. These specimens represent a challenge for the conventional X-ray CT due to large width-to-thickness aspect ratio. Large size of the panels prevents conventional CT scanning techniques from obtaining desired spatial resolution in the area susceptible to damage, which is typically of the size comparable to panel thickness.

Reliable defection of interlaminar defects requires reconstruction voxel size to be orders of magnitude smaller than the panel thickness.

TABLE 2

CT-scan parameters for the Carbon/Epoxy panel and hybrid composite panel.

|  | 401-mm Carbon/Epoxy panel | | 150-mm hybrid composite panel | |
| --- | --- | --- | --- | --- |
|  | Conventional method | Variable zoom method | Conventional method | Variable zoom method |
| Tube voltage, kV | 180 | 180 | 220 | 220 |
| Target current, µA | 90 | 90 | 70 | 70 |
| Magnification | 3x | 3x-10x | 8x | 8x-20x |
| Optimal voxel size, mm | 0.046 | 0.014 | 0.052 | 0.021 |
| Angular range, deg | 360 | 210 | 360 | 360 |
| Number of projections | 1200 | 820 | 1200 | 1200 |
| Detector pixel size, mm | 0.139 | 0.139 | 0.417 | 0.417 |

Each panel has a distinct material system typically encountered in the aerospace applications. The first panel is an IMT-Carbon/8552-Epoxy composite laminate; and the second panel is a hybrid IMT-Carbon and S2-Glass/913-Epoxy composite laminate. Both panels were manufactured by Boeing using the Hexcel prepregs. Table 2 details CT scan parameters used for evaluation and comparison of the Variable Zoom and conventional CT techniques.

Damage Detection in Carbon/Epoxy Composite Laminate

The first example demonstrates the Variable Zoom technique for the inspection of the impacted area in the Carbon/Epoxy panel. The width and thickness of the panel are 401 mm and 3.5 mm, respectively, resulting in width-to-thickness aspect ratio of 114.57. The panel is subjected to low-velocity impact damage approximately 4×4.5 mm$^2$ in area located in the middle of the panel.

FIG. 3 illustrates the change in the SOD for conventional and variable zoom trajectories. In the case of conventional scanning trajectory, the SOD remains constant and equals 265 mm resulting in 3× magnification that corresponds to the optimal spatial resolution of 46 µm. The SOD for the Variable Zoom trajectory varies from 81 to 265 mm using the sinusoidal path (Eq. 1), which leads to a maximum 10× magnification for the impacted area in the 401-mm Carbon/Epoxy specimen. The reconstruction voxel size is chosen for the highest magnification and equals 14 µm. We used the 210° angular range (known as short scan) for the Variable Zoom technique to reduce the acquisition time. The orbit was defined by Eq. (1) in the angular range $\theta \in [-105°, 105°]$ and SOD was set to 81 mm for $|\theta|<15°$.

Figure 19A:
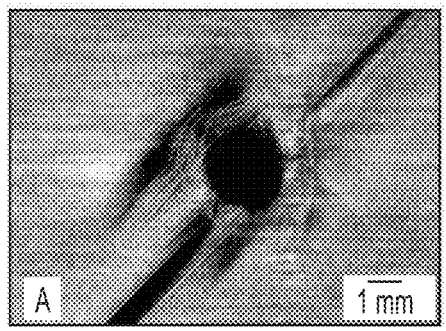
FIGS. 19A-19B show slices in a planar direction for variable zoom.
Figure 19B:
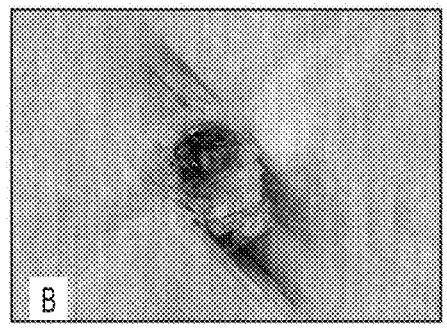
Figure 19C:
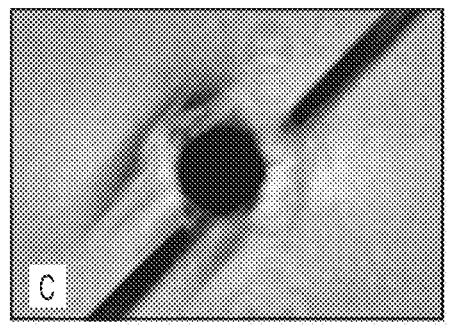
FIGS. 19C-19D show slices in a planar direction for the conventional method.
Figure 19D:
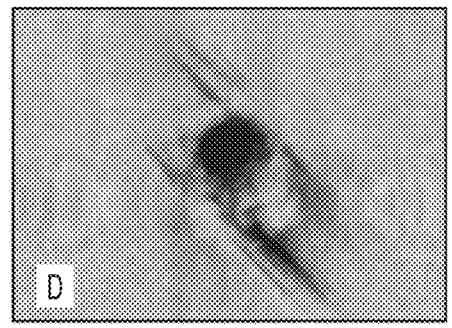

Qualitative analysis of reconstruction quality by Variable Zoom technique can be performed by examining slices at different through-the-thickness positions away from the damaged surface area as presented in FIGS. 19A-19D. The conventional acquisition mode provides images that lack sharpness as can be seen in FIGS. 19C-19D. Due to inadequate resolution, one cannot discriminate smaller matrix cracks. On the other hand, the Variable Zoom technique increases perceived spatial resolution, and the small size defects can be distinguished as shown in FIGS. 19A-19B.

Figure 20A:
FIGS. 20A-20B show slices in through-the-thickness direction for Variable Zoom and the conventional method, respectively.
Figure 20B:

The same trend emerges by inspecting slices at different depths as illustrated in FIGS. 20A-30B. Note that the improved sharpness and clarity of delamination reconstruction shown in FIG. 20A by the Variable Zoom technique is truly remarkable. Quality of through-the-thickness slices is strongly affected by lack of angular data leading to the detectable defects appearing smeared through a thickness range. In the spirit of this observation, a zooming technique is expected to improve resolution of planar slices shown in FIGS. 19A-19D but not necessarily of the thickness slices. Superior quality of the thickness slices obtained by the Variable Zoom technique is due to the weighting provided by Eq. (6).

To quantify differences in sharpness between the two methods we present the analysis of CT slices using variance estimation method described above. The boundaries of defects in both planar and thickness directions were identified by the contouring method. Ten slices adjacent to slices shown in FIGS. 19A-20B were used to find maximum of local variance measurements for each point on the contour.

Due to extreme complexity of defect boundaries, bigger windows include bigger percentage of boundary pixels than smaller windows, which leads to slower variance growth and increasing unsharpness estimations for bigger window sizes. Therefore, a comparison of variance values is more meaningful for complex defects. FIG. 21 shows normalized variance measurements for Variable Zoom and conventional CT reconstructions that use the same voxel size of 14 µm. Higher variance values for both planar and thickness direction slices by Variable Zoom indicate lower unsharpness of the reconstructed defects. For example, normalized variance of Variable Zoom planar sections $Var_n=0.83$ corresponds to the unsharpness of 2.6 pixels for window size w=10, while the unsharpness for conventional method is 8.8 pixels. FIG. 21 clearly indicates that Variable Zoom technique provides sharper resolution of defects than the conventional CT.

Damage Detection in Hybrid Composite Laminate

As a second example we applied the Variable Zoom technique to characterize the impact damage in a hybrid composite laminate. This material system imposes additional challenge due to large contrast variation between Carbon and Glass fibers. The laminate has width of 152 mm and thickness of 5.2 mm; the aspect ratio is 29.2; 3×3 mm$^2$ impact damage is in the center of the plate.

The scanning trajectories for this specimen are shown in FIG. 3. The SOD for the conventional acquisition is 100 mm, and the SOD for the Variable Zoom trajectory varies from 38 to 100 mm. Relatively low width-to-thickness ratio of the panel allows achieving 8× magnification; and Variable Zoom technique increases the magnification up to 20×. The reconstruction uses a 360° angular range and a reconstruction voxel size of 21 µm for both techniques.

It is evident that images obtained by the Variable Zoom technique show better sharpness as illustrated in FIGS. 22A-22D. Despite the relatively high magnification factor used in the conventional acquisition mode, the spatial resolution appears to be inadequate to provide desired reconstruction quality. On the other hand, variable magnification allows achieving higher spatial resolution leading to a better reconstruction quality. Again, note superior sharpness of thickness section reconstructed by the Variable Zoom technique shown in FIG. 22C.

This work demonstrated a novel X-ray Computed Tomography technique that is able to increase the spatial resolution for non-destructive inspection of plate-like objects with large in-plane dimensions relative to thickness. For instance, detection of damage in large composite plates can be identified as an important application of the proposed technique. The method incorporates two parts: a nonconventional trajectory of radiograph acquisition and a novel reconstruction weighting. Scanning trajectory includes simultaneous angular rotation and translation of a specimen towards the X-ray source as dimensions of a specimen permit. This technique increases magnification during scanning, and, as a result, the overall spatial resolution. Reconstruction is based on FDK method and incorporates radiograph weighting based on the distance from the panel to the X-ray source. Proposed method enables reconstructions with superior quality, and especially in the thickness direction.

Validation of the Variable Zoom technique for accurate dimensional measurements was demonstrated on the phantom models and on the CT scans of objects with measurable features. The estimated dimensions of a drilled hole in Carbon/Epoxy panel and Aluminum wires attached to the panel were in line with those obtained by mechanical measurements. In addition, quantitative assessment of the reconstructed detail sharpness demonstrated increased resolution of the defects by the Variable Zoom technique compared to the conventional CT. Finally, we performed a feasibility study on two composite laminate panels manufactured from different composite material systems and subjected to low-velocity impact loads. Both panels had relatively large thickness-to-width aspect ratio, which is a known challenge for a conventional CT scanning technique. In fact, the conventional CT method was not able to achieve the spatial resolution necessary to clearly differentiate smaller cracks and delaminations due to impact; while Variable Zoom technique was able to reconstruct volumes with higher spatial resolution leading to better sharpness of reconstructed slices, including significantly improved defect resolution in the thickness direction. These results were consistent for both material systems under investigation.

The Variable Zoom CT technique developed in this work has significant implications for NDI of materials and structures. On the materials side, this method can address the need in achieving the maximum resolution of a CT system without destroying a test article by cutting a small section that can be placed close enough to the X-ray source for sufficient geometric magnification. There is a similar need for structures that can fit into existing CT system enclosures but are subject to small flaws with critical features in three dimensions that are not recognizable using the conventional scanning techniques. Also, the new method offers additional flexibility towards enabling high-resolution CT for larger structures currently not suitable for microfocus CT systems.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

REFERENCE LIST A

[1] A. Makeev, G. Seon, Y. Nikishkov, D. Nguyen, P. Mathews, M. Robeson, Analysis Methods Improving Confidence in Material Qualification for Laminated Composites, J. Am. Helicopter Soc. 64 (2019) 1-13.

[2] G. Seon, A. Makeev, Y. Nikishkov, E. Lee, Effects of defects on interlaminar tensile fatigue behavior of carbon/epoxy composites, Compos. Sci. Technol. 89 (2013) 194-201.

[3] Y. Nikishkov, G. Seon, A. Makeev, Structural analysis of composites with porosity defects based on X-ray computed tomography, J. Compos. Mater. 48 (2014) 2131-2144.

[4] J. Varna, R. Joffe, L. A. Berglund, Effect of voids on failure mechanisms in RTM laminates, Compos. Sci. Technol. 53 (1995) 241-249.

[5] G. Seon, A. Makeev, Structures Perspective for Strength and Fatigue Prognosis in Composites with Manufacturing Irregularities, J. Am. Helicopter Soc. 60 (2015) 1-10.

[6] M. Wisnom, T. Reynolds, N. Gwilliam, Reduction in interlaminar shear strength by discrete and distributed voids, Compos. Sci. Technol. 56 (1996) 93-101.

[7] P. J. Withers, M. Preuss, Fatigue and damage in structural materials studied by X-ray tomography, Annu. Rev. Mater. Res. 42 (2012) 81-103.

[8] S. M. Spearing, I. Sinclair, The micro-mechanics of strength, durability and damage tolerance in composites: new insights from high resolution computed tomography, IOP conference Series: Mater. Sci. Eng. 139 (1) (2016).

[9] J. Lambert, A. R. Chambers, I. Sinclair, S. M. Spearing, 3D damage characterisation and the role of voids in the fatigue of wind turbine blade materials, Compos. Sci. Technol. 72 (2012) 337-343.

[10] Y. Nikishkov, L. Airoldi, A. Makeev, Measurement of voids in composites by X-ray Computed Tomography, Compos. Sci. Technol. 89 (2013) 89-97.

[11] Y. Wang, C. S. Garcea, P. J. Withers, Computed Tomography of Composites, in: C. H. Zweben, P. Beaumont (Eds.), Compr. Compos. Mater. II, 2nd ed., Elsevier, 2018: pp. 101-118.

[12] W. A. Kalender, Computed Tomography, Publicis Publishing, Erlangen, 2011.

[13] J. Stein, C. Soutis, P. J. Withers, The quantification of impact damage distribution in composite laminates by analysis of X-ray computed tomograms, Compos. Sci. Technol. 152 (2018) 139-148.

[14] J. Rouse, R. Bradley, P. J. Withers, Imaging impact damage in high aspect ratio composite plates, in: 18th Int. Conf. Compos. Mater., 2011.

[15] D. J. Bull, L. Helfen, I. Sinclair, S. M. Spearing, T. Baumbach, A comparison of multi-scale 3D X-ray tomographic inspection techniques for assessing carbon fibre composite impact damage, Compos. Sci. Technol. 75 (2013) 55-61.

[16] Quinto, E. T. "Singularities of the X-ray transform and limited data tomography in R2 and R3," SIAM J. Math. Analysis 24 (1993) 1215-1225.

[17] J. Zhou, M. Maisl, H. Reiter, W. Arnold, Computed laminography for materials testing, Appl. Phys. Lett. 68 (1996) 3500-3502.

[18] F. Xu, L. Helfen, T. Baumbach, H. Suhonen, Comparison of image quality in computed laminography and tomography, Opt. Soc. Am. 20 (2012) 361-366.

[19] L. Helfen, F. Xu, H. Suhonen, P. Cloetens, and T. Baumbach. Laminographic imaging using synchrotron radiation—challenges and opportunities. J. of Phys.: Conf. Ser. 425 192025 (2013).

[20] S. L. Fisher, D. J. Holmes, J. S. Jørgensen, P. Gajjar, J. Behnsen, W. R. B. Lionheart, P. J. Withers, Laminography in the lab: imaging planar objects using a conventional x-ray CT scanner, Meas. Sci. Technol. 30 (2019) 1-13.

[21] L. Helfen, A. Myagotin, A. Rack, P. Pernot, P. Mikulik, M. Di Michiel, T. Baumbach, Synchrotron-radiation computed laminography for high-resolution three-dimensional imaging of flat devices, Phys. Status Solidi A Appl. Mater. Sci. 204 (2007) 2760-2765.

[22] N. S. O. Brien, R. P. Boardman, I. Sinclair, T. Blumensath, Recent Advances in X-ray Cone-beam Computed Laminography, J. Xray. Sci. Technol. 24 (2016) 691-707.

[23] C. E. Wood, N. S. O'Brien, A. Denysov, T. Blumensath, Computed Laminography of CFRP using an X-ray Cone Beam and Robotic Sample Manipulator Systems, IEEE Trans. Nucl. Sci. 67 (2018) 1384-1393.

[24] H. Yu, Q. Xu, X. Mou, G. Wang, Recent Progress in Local Reconstruction, in: Proc. SPIE, San Diego, CA, USA, 2010: pp. 1-14.

[25] X. Xiao, F. De Carlo, S. Stock, Practical error estimation in zoom-in and truncated tomography reconstructions, Rev. Sci. Instrum. 78 (2007) 063705.

[26] A. Dabravolski, K. J. Batenburg, J. Sijbers, Adaptive zooming in X-ray computed tomography, J. Xray. Sci. Technol. 22 (2014) 77-89.

[27] Hexcel Corporation, HexPly® 8552 product data sheet. hexcel.com/user_area/content_media/raw/HexPly_8552_us_DataSheet.pdf, 2016 (accessed Aug. 6, 2019).

[28] Hexcel Corporation, HexPly® 913 257° F. (125° C.) product data sheet. hexcel.com/user_area/content_media/raw/HexPly_913_us_DataSheet.pdf, 2016 (accessed Aug. 6, 2019).

[29] Shimadzu Corporation, inspeXio SMX-225CT FPT HD Instruction Manual, 2017.

[30] L. A. Feldkamp, L. C. Davis, J. W. Kress, Practical cone-beam algorithm, Opt. Soc. Am. 1 (1984) 612-619.

[31] A. C. Kak, M. Slaney, Principles of Computerized Tomographic Imaging, IEEE Press, New York, NY, 1988.

[32] SciPy.org, Discrete Fourier Transform (numpy.fft), docs.scipy.org/doc/numpy/reference/routines.fft.html, 2019 (accessed Aug. 6, 2019).

[33] L. Moisan, Periodic Plus Smooth Image Decomposition, J. Math. Imaging Vis. 39 (2011) 161-179.

[34] B. De Man, S. Basu, Distance-driven projection and backprojection in three dimensions, Phys. Med. Biol. 49 (2004) 2463-2475.

[35] Y. Long, J. A. Fessler, J. M. Balter, 3D forward and back-projection for X-ray CT using separable footprints, IEEE Trans. Med. Imaging. 29 (2010) 1839-1850.

[36] A. Kraemer, E. Kovacheva, G. Lanza, Projection based evaluation of CT image quality in dimensional metrology, in: Digit. Ind. Radiol. Comput. Tomogr., 2015: pp. 1-10.

What is claimed is:

1. A variable zoom method of an X-ray computed tomography (CT) scanner, the method comprising:

emitting an X-ray beam from an X-ray source to project a region of interest (ROI) of a specimen within a field of view (FOV) onto a detector;

obtaining projections of the ROI of the specimen with the detector while rotating the specimen about a rotational axis of a specimen stage and translating the specimen stage along an acquisition trajectory between the X-ray source and the detector; and reconstructing, by a reconstruction computer, a three-dimensional volume of the specimen from the projections scanned by the detector, wherein the acquisition trajectory specifies a source-to-object distance (SOD) between the X-ray source and the rotational axis of the specimen stage at each rotation angle of the specimen stage.

2. The method of claim 1, wherein the X-ray source and the detector are stationary while rotating and translating the specimen.

3. The method of claim 1, wherein the ROI is projected onto a central area of the detector.

4. The method of claim 1, wherein the acquisition trajectory translates the rotational axis of the specimen stage along a center of the FOV.

5. The method of claim 1, wherein an initial SOD along the acquisition trajectory is $SOD_{ROI}$, wherein the $SOD_{ROI}$ is a closest SOD at which the ROI is fully within the FOV.

6. The method of claim 5, wherein the $SOD_{ROI}$ is a closest SOD at which the ROI remains within the FOV while a rotation angle of the specimen stage is less than a threshold angle.

7. The method of claim 6, wherein the SOD at each rotation angle of the specimen stage is:

$$SOD(\theta) = \max\{SOD_{ROI}, S_0 + \tfrac{1}{2}(T_P + (S_P - T_P)|\sin\theta|)\},$$

where $\theta$ is the rotation angle of the specimen stage, $SOD(\theta)$ is the SOD at each rotation angle of the specimen stage, $SOD_{ROI}$ is the initial SOD, $S_0$ is a safety offset, $S_P$ is a specimen width, and $T_P$ is a specimen thickness.

8. The method of claim 7, wherein $SOD(\theta) = SOD_{ROI}$ while the rotation angle of the specimen stage is less than the threshold angle.

9. The method of claim 1, wherein reconstructing the three-dimensional volume comprises:

weighting a backprojection of a set of filtered radiographs with a weighting factor based on the SOD at each rotation angle of the specimen stage.

10. The method of claim 9, wherein the weighting factor comprises:

$$w^{vz}(\theta) = \frac{SOD(\theta)}{SDD},$$

where $w^{vz}$ is the weighting factor, $SOD(\theta)$ is the SOD at each rotation angle of the specimen stage, and SDD is a source-to-detector distance.

11. The method of claim 9, wherein reconstructing the three-dimensional volume further comprises:

calculating a projection to volume transformation for each projection angle and the SOD to produce the backprojection of the set of filtered radiographs; and adding weighted backprojected pixel values to voxels in the three-dimensional volume based on an interpolation method to produce the reconstruction of the three-dimensional volume.

12. The method of claim 11, wherein reconstructing the three-dimensional volume further comprises:
   calculating a ramp filter in the frequency domain;
   calculating weighted and filtered radiographs based on the ramp filter and applying a periodic-smooth decomposition to produce the set of filtered radiographs.

13. The method of claim 12, wherein calculating the ramp filter in the frequency domain comprises calculating a one-dimensional direct Fourier Transform on:

$$h[np_x] = \frac{1}{(2p_x)^2} \begin{cases} 1, & n = 0 \\ 0, & n \text{ even} \\ -1/(\pi n/2)^2, & n \text{ odd} \end{cases}$$

where n is and integer $n \in [-n_x^{zp}, n_x^{zP})$, $p_x$ is a row pixel spacing, $n_x^{zp} = (2n_x - 1)_2$ rounded to the next power of two, and $n_x$ is a number of pixels in a projection row.

14. The method of claim 11, wherein when calculating the projection to volume transformation, projection coordinates are different for each projection angle according to varying $SOD(\theta)$.

15. The method of claim 14, wherein calculating the projection to volume transformation comprises:
   calculating a three-dimensional coordinate transformation $(x, y, z)^T = R(\theta) R_V (t, s, r)^T$, where (t, s, r) are reconstructed volume coordinates, (x, y, z) are projection coordinates, $R_V$ is a volume transformation matrix and $R_\theta$ is a matrix of specimen rotation.

16. The method of claim 11, wherein the interpolation method is a distance-driven method or a separable footprints method.

17. The method of claim 11, wherein the weighted and filtered radiographs are weighted to account for different ray lengths in a cone X-ray beam.

18. The method of claim 17, wherein calculating the weighted and filtered radiographs and applying the periodic-smooth decomposition comprises calculating:

$$S_\theta(x, y_k) = [P'_\theta(x, y_k) * h(x)] = p_x IFFT\{FFTP'_\theta(x, y_k)_{ZP} \cdot FFTh[np_x]_{shift}\},$$

and $$P'_\theta(x, y_k) = PS\left[\frac{P_\theta(x, y_k)}{\sqrt{1 + (x^2 + y_k^2)/SOD^2(\theta)}}\right],$$

where FFT is a one-dimensional direct Fourier transform, IFFT is a one-dimensional inverse discrete Fourier transform, $h[np_x]_{shift}$ is a half-spaces of the ramp filter $h[np_x]$ swapped using a fftshift method, $n_x^{zp}$ is a zero-padded radiograph to avoid inter-period artefacts, and PS is the periodic-smooth decomposition such that only a periodic part of a weighted radiograph boundary is used.

19. The method of claim 11, wherein adding the weighted backprojected pixel values to voxels in the three-dimensional volume based on an interpolation method comprises calculating:

$$v(t,s,r) = \Sigma_\theta w^{vz}(\theta) z_d^2(\theta) S_\theta(xz_d, yz_d),$$

where $$z_d(\theta) = \frac{1}{1 - z/SOD(\theta)},$$

v(t, s, r) is a reconstruction volume value, the summation is calculated for all coordinate triads (t, s, r), interpolated values v(t, s, r) are obtained using the interpolation method, $w^{vz}(\theta)$ is the weighting factor, and $S_\theta(xz_d, yz_d)$ are filtered radiographs.

* * * * *

UNITED STATES PATENT AND TRADEMARK OFFICE
CERTIFICATE OF CORRECTION

| | | |
|---|---|---|
| PATENT NO. | : 12,130,245 B2 | Page 1 of 1 |
| APPLICATION NO. | : 17/766637 | |
| DATED | : October 29, 2024 | |
| INVENTOR(S) | : Andrew Makeev et al. | |

It is certified that error appears in the above-identified patent and that said Letters Patent is hereby corrected as shown below:

In the Claims

Column 32, Claim 18, Lines 1-3, reading:
The method of claim 17, wherein calculating the weighted and filtered radiographs and applying the periodic-smooth decomposition comprises calculating:…

Should Read:
The method of claim 12, wherein calculating the weighted and filtered radiographs and applying the periodic-smooth decomposition comprises calculating:…

Signed and Sealed this
Twenty-fifth Day of February, 2025

Coke Morgan Stewart
*Acting Director of the United States Patent and Trademark Office*